(12) United States Patent
Mahony et al.

(10) Patent No.: US 10,835,594 B2
(45) Date of Patent: Nov. 17, 2020

(54) TYPE III SECRETION INJECTISOME PROTEINS FOR TREATMENT AND PREVENTION OF CHLAMYDIAL INFECTIONS

(71) Applicant: McMaster University, Hamilton (CA)

(72) Inventors: James B. Mahony, Oakville (CA); David C. Bulir, Hamilton (CA); Christopher B. Stone, Courtice (CA)

(73) Assignee: McMaster University, Ontario (CA)

( * ) Notice: Subject to any disclaimer, the term of this patent is extended or adjusted under 35 U.S.C. 154(b) by 100 days.

(21) Appl. No.: 15/111,944

(22) PCT Filed: Jan. 16, 2015

(86) PCT No.: PCT/CA2015/000030
§ 371 (c)(1),
(2) Date: Jul. 15, 2016

(87) PCT Pub. No.: WO2015/106345
PCT Pub. Date: Jul. 23, 2015

(65) Prior Publication Data
US 2016/0346375 A1    Dec. 1, 2016

Related U.S. Application Data

(60) Provisional application No. 61/928,117, filed on Jan. 16, 2014.

(51) Int. Cl.
*A61K 39/118*    (2006.01)
*C07K 14/295*    (2006.01)
*A61K 39/00*    (2006.01)

(52) U.S. Cl.
CPC .......... *A61K 39/118* (2013.01); *C07K 14/295* (2013.01); *A61K 2039/545* (2013.01); *A61K 2039/55561* (2013.01); *A61K 2039/55577* (2013.01); *A61K 2039/70* (2013.01)

(58) Field of Classification Search
None
See application file for complete search history.

(56) References Cited

U.S. PATENT DOCUMENTS

| | | |
|---|---|---|
| 2006/0034871 A1 | 2/2006 | Grandi et al. |
| 2009/0274701 A1 | 11/2009 | Griffais et al. |
| 2009/0274719 A1 | 11/2009 | Griffais et al. |

FOREIGN PATENT DOCUMENTS

| | | | |
|---|---|---|---|
| EP | 2386314 A1 | 11/2011 | |
| WO | 99/28475 A2 | 6/1999 | |
| WO | WO-9927105 A2 * | 6/1999 | ........... C07K 14/295 |
| WO | 2006/045308 A2 | 5/2006 | |

OTHER PUBLICATIONS

Ellis (Vaccines, W.B. Saunders Company, Chapter 29, 1988, pp. 568-574).*
Boslego et al (Vaccines and Immunotherapy, 1991, Chapter 17).*
Skolnick et al. (Trends in Biotechnology 18: 34-39, 2000).*
Fields K.A., and Hackstadt T. Evidence for the secretion of Chlamydia trachomatis CopN by a type III secretion mechanism. 2000. Molecular Microbiology, 38(5): 1048-1060.
Johnson D.L., Stone C.B., Mahony J.B. Interactions between CdsD, CdsQ, and CdsL, three putative Chlamydophila pneumoniae type III secretion proteins. Journal of Bacteriology, Apr. 2008;190(8):2972-80. Epub Feb. 15, 2008.
Stone C.B., Johnson D.L., Bulir D.C., Gilchrist J.D., Mahony J.B. Characterization of the putative type III secretion ATPase Cd (Cpn0707) of Chlamydophila pneumoniae. Journal of Bacteriology, Oct. 2008;190(20):6580-8. Epub Aug. 15, 2008.
Stone C.B., Bulir D.C., Emdin C.A., Pirie R.M., Porfilio E.A., Slootstra J.W., Mahony J.B. Chlamydia Pneumoniae CdsL Regulates CdsN ATPase Activity, and Disruption with a Peptide Mimetic Prevents Bacterial Invasion. Frontiers in Microbiology, 2011;2:21. Epub Feb. 14, 2011.
Markham A.P., Jaafar Z.A., Kemege K.E., Middaugh C.R., Hefty P.S. Biophysical characterization of Chlamydia trachomatis CT584 supports its potential role as a type III secretion needle tip protein. Biochemistry. Nov. 3, 2009;48 (43):10353-61.
Stone C.B., Sugiman-Marangos S., Bulir D.C., Clayden R.C., Leighton T.L., Slootstra J.W., Junop M.S., Mahony J.B. Structural Characterization of a novel Chlamydia pneumoniae type III secretion-associated protein, Cpn0803. PLoS One. 2012;7(1):e30220. Epub Jan. 17, 2012.

* cited by examiner

*Primary Examiner* — Robert A Zeman
(74) *Attorney, Agent, or Firm* — Bereskin & Parr LLP/S.E.N.C.R.L., s.r.l.; Micheline Gravelle; Ainslie Parsons

(57) ABSTRACT

Cpn0803, CopB (Cpn0809) and CopD (Cpn0808) proteins and homologues thereof are shown to induce an immune response that is protective against a live challenge with *Chlamydia*. Methods and uses of Cpn0803 or fragments or epitopes thereof alone or together with CopB and/or CopD or fragments or epitopes thereof for treating or preventing chlamydial infection in a subject in need thereof are provided.

Figure 1:
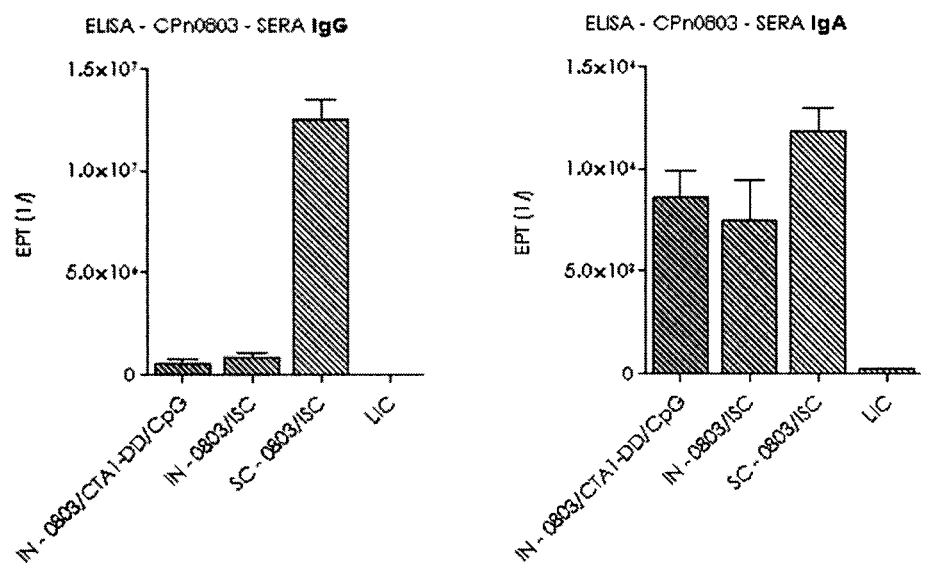

5 Claims, 22 Drawing Sheets
Specification includes a Sequence Listing.

Cpg+Antigen Vaccinated Mouse

PBS Vaccinated Mouse

SEQUENCE LISTING

```
<160> NUMBER OF SEQ ID NOS: 6

<210> SEQ ID NO 1
<211> LENGTH: 184
<212> TYPE: PRT
<213> ORGANISM: Chlamydia pneumoniae
```

<400> SEQUENCE: 1

```
Met Ala Ala Lys Thr Lys Thr Leu Glu Leu Glu Asp Asn Val Phe Leu
1               5                   10                  15

Leu Leu Glu Gly Asn Leu Lys Arg Ile Phe Ala Thr Pro Ile Gly Tyr
            20                  25                  30

Thr Thr Phe Arg Glu Phe Gln Asn Val Val Phe Asn Cys Ala Asn Gly
        35                  40                  45

Gln Gln Glu Ile Ala Asn Phe Phe Glu Met Leu Ile Asn Gly Lys
    50                  55                  60

Leu Thr Gln Glu Leu Ala Pro Gln Gln Lys Gln Ala Ala His Ser Leu
65                  70                  75                  80

Ile Ala Glu Phe Met Met Pro Ile Arg Val Ala Lys Asp Ile His Glu
                85                  90                  95

Arg Gly Glu Phe Ile Asn Phe Ile Thr Ser Asp Met Leu Thr Gln Gln
            100                 105                 110

Glu Arg Cys Ile Phe Leu Asn Arg Leu Ala Arg Val Asp Gly Gln Glu
        115                 120                 125

Phe Leu Leu Met Thr Asp Val Gln Asn Thr Cys His Leu Ile Arg His
130                 135                 140

Leu Leu Ala Arg Leu Leu Glu Ala Gln Lys Asn Pro Val Gly Glu Lys
145                 150                 155                 160

Asn Leu Gln Glu Ile Gln Glu Ile Thr Ser Leu Lys Asn His Phe
            165                 170                 175

Asp Glu Leu Thr Lys Ala Leu Gln
            180
```

<210> SEQ ID NO 2
<211> LENGTH: 490
<212> TYPE: PRT
<213> ORGANISM: Chlamydia pneumoniae

<400> SEQUENCE: 2

```
Met Ser Ile Ser Ser Ser Gly Pro Asp Asn Gln Lys Asn Ile Met
1               5                   10                  15

Ser Gln Val Leu Thr Ser Thr Pro Gln Gly Val Pro Gln Gln Asp Lys
            20                  25                  30

Leu Ser Gly Asn Glu Thr Lys Gln Ile Gln Gln Thr Arg Gln Gly Lys
        35                  40                  45

Asn Thr Glu Met Glu Ser Asp Ala Thr Ile Ala Gly Ala Ser Gly Lys
    50                  55                  60

Asp Lys Thr Ser Ser Thr Thr Lys Thr Glu Thr Ala Pro Gln Gln Gly
65                  70                  75                  80

Val Ala Ala Gly Lys Glu Ser Ser Glu Ser Gln Lys Ala Gly Ala Asp
                85                  90                  95

Thr Gly Val Ser Gly Ala Ala Thr Thr Ala Ser Asn Thr Ala Thr
            100                 105                 110

Lys Ile Ala Met Gln Thr Ser Ile Glu Glu Ala Ser Lys Ser Met Glu
        115                 120                 125

Ser Thr Leu Glu Ser Leu Gln Ser Leu Ser Ala Gln Met Lys Glu
130                 135                 140

Val Glu Ala Val Val Ala Ala Leu Ser Gly Lys Ser Ser Gly Ser
145                 150                 155                 160

Ala Lys Leu Glu Thr Pro Glu Leu Pro Lys Pro Gly Val Thr Pro Arg
            165                 170                 175
```

```
Ser Glu Val Ile Glu Ile Gly Leu Ala Leu Ala Lys Ala Ile Gln Thr
            180                 185                 190

Leu Gly Glu Ala Thr Lys Ser Ala Leu Ser Asn Tyr Ala Ser Thr Gln
        195                 200                 205

Ala Gln Ala Asp Gln Thr Asn Lys Leu Gly Leu Glu Lys Gln Ala Ile
    210                 215                 220

Lys Ile Asp Lys Glu Arg Glu Tyr Gln Glu Met Lys Ala Ala Glu
225                 230                 235                 240

Gln Lys Ser Lys Asp Leu Glu Gly Thr Met Asp Thr Val Asn Thr Val
                245                 250                 255

Met Ile Ala Val Ser Val Ala Ile Thr Val Ile Ser Ile Val Ala Ala
            260                 265                 270

Ile Phe Thr Cys Gly Ala Gly Leu Ala Gly Leu Ala Ala Gly Ala Ala
        275                 280                 285

Val Gly Ala Ala Ala Gly Gly Ala Ala Gly Ala Ala Ala Ala Thr
    290                 295                 300

Thr Val Ala Thr Gln Ile Thr Val Gln Ala Val Val Gln Ala Val Lys
305                 310                 315                 320

Gln Ala Val Ile Thr Ala Val Arg Gln Ala Ile Thr Ala Ala Ile Lys
                325                 330                 335

Ala Ala Val Lys Ser Gly Ile Lys Ala Phe Ile Lys Thr Leu Val Lys
            340                 345                 350

Ala Ile Ala Lys Ala Ile Ser Lys Gly Ile Ser Lys Val Phe Ala Lys
        355                 360                 365

Gly Thr Gln Met Ile Ala Lys Asn Phe Pro Lys Leu Ser Lys Val Ile
    370                 375                 380

Ser Ser Leu Thr Ser Lys Trp Val Thr Gly Val Gly Val Val
385                 390                 395                 400

Ala Ala Pro Ala Leu Gly Lys Gly Ile Met Gln Met Gln Leu Ser Glu
                405                 410                 415

Met Gln Gln Asn Val Ala Gln Phe Gln Lys Glu Val Gly Lys Leu Gln
            420                 425                 430

Ala Ala Ala Asp Met Ile Ser Met Phe Thr Gln Phe Trp Gln Gln Ala
        435                 440                 445

Ser Lys Ile Ala Ser Lys Gln Thr Gly Glu Ser Asn Glu Met Thr Gln
    450                 455                 460

Lys Ala Thr Lys Leu Gly Ala Gln Ile Leu Lys Ala Tyr Ala Ala Ile
465                 470                 475                 480

Ser Gly Ala Ile Ala Gly Ala His Lys Thr
                485                 490

<210> SEQ ID NO 3
<211> LENGTH: 444
<212> TYPE: PRT
<213> ORGANISM: Chlamydia pneumoniae

<400> SEQUENCE: 3

Met Thr Ser Gly Val Ser Gly Ser Ser Gln Asp Pro Thr Leu Ala
1               5                   10                  15

Ala Gln Leu Ala Gln Ser Ser Gln Lys Ala Gly Asn Ala Gln Ser Gly
            20                  25                  30

His Asp Thr Lys Asn Val Thr Lys Gln Gly Ala Gln Ala Glu Val Ala
        35                  40                  45

Ala Gly Gly Phe Glu Asp Leu Ile Gln Asp Ala Ser Ala Gln Ser Thr
```

```
                    50                  55                  60
Gly Lys Lys Glu Ala Thr Ser Thr Thr Lys Ser Ser Lys Gly Glu
 65                  70                  75                  80

Lys Ser Glu Lys Ser Gly Lys Ser Lys Ser Ser Thr Ser Val Ala Ser
                     85                  90                  95

Ala Ser Glu Thr Ala Thr Ala Gln Ala Val Gln Gly Pro Lys Gly Leu
                    100                 105                 110

Arg Gln Asn Asn Tyr Asp Ser Pro Ser Leu Pro Thr Pro Glu Ala Gln
                    115                 120                 125

Thr Ile Asn Gly Ile Val Leu Lys Lys Gly Met Gly Thr Leu Ala Leu
130                 135                 140

Leu Gly Leu Val Met Thr Leu Met Ala Asn Ala Ala Gly Glu Ser Trp
145                 150                 155                 160

Lys Ala Ser Phe Gln Ser Gln Asn Gln Ala Ile Arg Ser Gln Val Glu
                    165                 170                 175

Ser Ala Pro Ala Ile Gly Glu Ala Ile Lys Arg Gln Ala Asn His Gln
                    180                 185                 190

Ala Ser Ala Thr Glu Ala Gln Ala Lys Gln Ser Leu Ile Ser Gly Ile
                    195                 200                 205

Val Asn Ile Val Gly Phe Thr Val Ser Val Gly Ala Gly Ile Phe Ser
210                 215                 220

Ala Ala Lys Gly Ala Thr Ser Ala Leu Lys Ser Ala Ser Phe Ala Lys
225                 230                 235                 240

Glu Thr Gly Ala Ser Ala Ala Gly Gly Ala Ala Ser Lys Ala Leu Thr
                    245                 250                 255

Ser Ala Ser Ser Ser Val Gln Gln Thr Met Ala Ser Thr Ala Lys Ala
                    260                 265                 270

Ala Thr Thr Ala Ala Ser Ser Ala Gly Ser Ala Ala Thr Lys Ala Ala
                    275                 280                 285

Ala Asn Leu Thr Asp Asp Met Ala Ala Ala Ser Lys Met Ala Ser
                    290                 295                 300

Asp Gly Ala Ser Lys Ala Ser Gly Gly Leu Phe Gly Glu Val Leu Asn
305                 310                 315                 320

Lys Pro Asn Trp Ser Glu Lys Val Ser Arg Gly Met Asn Val Lys
                    325                 330                 335

Thr Gln Gly Ala Arg Val Ala Ser Phe Ala Gly Asn Ala Leu Ser Ser
                    340                 345                 350

Ser Met Gln Met Ser Gln Leu Met His Gly Leu Thr Ala Ala Val Glu
                    355                 360                 365

Gly Leu Ser Ala Gly Gln Thr Gly Ile Glu Val Ala His His Gln Arg
                    370                 375                 380

Leu Ala Gly Gln Ala Glu Ala Gln Ala Glu Val Leu Lys Gln Met Ser
385                 390                 395                 400

Ser Val Tyr Gly Gln Gln Ala Gly Gln Ala Gly Gln Leu Gln Glu Gln
                    405                 410                 415

Ala Met Gln Ser Phe Asn Thr Ala Leu Gln Thr Leu Gln Asn Ile Ala
                    420                 425                 430

Asp Ser Gln Thr Gln Thr Thr Ser Ala Ile Phe Asn
                    435                 440

<210> SEQ ID NO 4
<211> LENGTH: 183
<212> TYPE: PRT
<213> ORGANISM: Chlamydia trachomatis
```

<400> SEQUENCE: 4

```
Met Thr Thr Lys Pro Lys Thr Leu Glu Ile Asp Asn Asn Thr Phe Leu
1               5                   10                  15

Leu Leu Glu Gly Asn Leu Lys Arg Ile Phe Ala Thr Pro Ile Gly Tyr
            20                  25                  30

Thr Thr Phe Arg Glu Phe Gln Asn Val Val Phe Asn Cys Ala Gln Gly
        35                  40                  45

Gln Gln Glu Leu Ala Asn Phe Leu Phe Glu Met Leu Ile Asn Gly Lys
    50                  55                  60

Leu Leu Gln Glu Leu Pro Ala Gly Gln Lys Gln Ser Ala Gln Ser Leu
65                  70                  75                  80

Ile Val Gln Phe Met Met Pro Ile Arg Val Ala Lys Asp Ile His Glu
                85                  90                  95

Arg Gly Glu Phe Ile Asn Phe Ile Thr Ser Asp Met Leu Ala Gln Gln
            100                 105                 110

Glu Arg Cys Val Phe Leu Asn Arg Leu Ser Arg Val Asp Gly Gln Glu
        115                 120                 125

Phe Leu Leu Met Thr Asp Val Gln Asn Thr Cys His Leu Ile Arg His
    130                 135                 140

Leu Leu Ser Arg Leu Leu Glu Ala Gln Lys Asn Pro Ile Gly Glu Lys
145                 150                 155                 160

Asn Leu Gln Glu Ile Gln Glu Asp Leu Asp Ser Leu Arg Ala His Phe
                165                 170                 175

Glu Glu Leu Thr Lys Ser Val
            180
```

<210> SEQ ID NO 5
<211> LENGTH: 487
<212> TYPE: PRT
<213> ORGANISM: Chlamydia trachomatis

<400> SEQUENCE: 5

```
Met Ser Leu Ser Ser Ser Ser Ser Asp Ser Ser Asn Leu Lys Asn
1               5                   10                  15

Val Leu Ser Gln Val Ile Ala Ser Thr Pro Gln Gly Val Pro Asn Ala
            20                  25                  30

Asp Lys Leu Thr Asp Asn Gln Val Lys Gln Val Gln Thr Arg Gln
        35                  40                  45

Asn Arg Asp Asp Leu Ser Met Glu Ser Asp Val Ala Val Ala Gly Thr
    50                  55                  60

Ala Gly Lys Asp Arg Ala Ala Ser Ala Ser Gln Ile Glu Gly Gln Glu
65                  70                  75                  80

Leu Ile Glu Gln Gln Gly Leu Ala Ala Gly Lys Glu Thr Ala Ser Ala
                85                  90                  95

Asp Ala Thr Ser Leu Thr Gln Ser Ala Ser Lys Gly Ala Ser Ser Gln
            100                 105                 110

Gln Cys Ile Glu Asp Thr Ser Lys Ser Leu Glu Leu Ser Ser Leu Ser
        115                 120                 125

Ser Leu Ser Ser Val Asp Ala Thr His Leu Gln Glu Ile Gln Ser Ile
    130                 135                 140

Val Ser Ser Ala Met Gly Ala Thr Asn Glu Leu Ser Leu Thr Asn Leu
145                 150                 155                 160

Glu Thr Pro Gly Leu Pro Lys Pro Ser Thr Thr Pro Arg Gln Glu Val
                165                 170                 175
```

```
Met Glu Ile Ser Leu Ala Leu Ala Lys Ala Ile Thr Ala Leu Gly Glu
            180                 185                 190

Ser Thr Gln Ala Ala Leu Glu Asn Phe Gln Ser Thr Gln Ser Gln Ser
            195                 200                 205

Ala Asn Met Asn Lys Met Ser Leu Glu Ser Gln Gly Leu Lys Ile Asp
        210                 215                 220

Lys Glu Arg Glu Glu Phe Lys Lys Met Gln Glu Ile Gln Gln Lys Ser
225                 230                 235                 240

Gly Thr Asn Ser Thr Met Asp Thr Val Asn Lys Val Met Ile Gly Val
                245                 250                 255

Thr Val Ala Ile Thr Val Ile Ser Val Val Ser Ala Leu Phe Thr Cys
            260                 265                 270

Gly Leu Gly Leu Ile Gly Thr Ala Ala Gly Ala Thr Ala Ala Ala
            275                 280                 285

Ala Gly Ala Thr Ala Ala Ala Thr Thr Ala Thr Ser Val Ala Thr Thr
        290                 295                 300

Val Ala Thr Gln Val Thr Met Gln Ala Val Val Gln Val Val Lys Gln
305                 310                 315                 320

Ala Ile Ile Gln Ala Val Lys Gln Ala Ile Val Gln Ala Ile Lys Gln
                325                 330                 335

Gly Ile Lys Gln Gly Ile Lys Gln Ala Ile Lys Gln Ala Val Lys Ala
            340                 345                 350

Ala Val Lys Thr Leu Ala Lys Asn Val Gly Lys Ile Phe Ser Ala Gly
            355                 360                 365

Lys Asn Ala Val Ser Lys Ser Phe Pro Lys Leu Ser Lys Val Ile Asn
        370                 375                 380

Thr Leu Gly Ser Lys Trp Val Thr Leu Gly Val Gly Ala Leu Thr Ala
385                 390                 395                 400

Val Pro Gln Leu Val Ser Gly Ile Thr Ser Leu Gln Leu Ser Asp Met
                405                 410                 415

Gln Lys Glu Leu Ala Gln Ile Gln Lys Glu Val Gly Ala Leu Thr Ala
            420                 425                 430

Gln Ser Glu Met Met Lys Ala Phe Thr Leu Phe Trp Gln Gln Ala Ser
            435                 440                 445

Lys Ile Ala Ala Lys Gln Thr Glu Ser Pro Ser Glu Thr Gln Gln Gln
        450                 455                 460

Ala Ala Lys Thr Gly Ala Gln Ile Ala Lys Ala Leu Ser Ala Ile Ser
465                 470                 475                 480

Gly Ala Leu Ala Ala Ala Ala
                485

<210> SEQ ID NO 6
<211> LENGTH: 439
<212> TYPE: PRT
<213> ORGANISM: Chlamydia trachomatis

<400> SEQUENCE: 6

Met Thr Thr Gly Val Arg Gly Asp Asn Ala Pro Asp Pro Ser Leu Leu
1               5                   10                  15

Ala Gln Leu Thr Gln Asn Ala Asn Ser Ala Ser Ala Ala Ser Thr Gly
            20                  25                  30

Lys Asn Gly Gln Val Ala Gly Ala Lys Gln Glu Asn Val Asp Ala Ser
        35                  40                  45

Phe Glu Asp Leu Leu Gln Asp Ala Gln Gly Thr Gly Gly Ser Lys Lys
```

```
                50              55              60
Ala Thr Ala Asn Gln Thr Ser Lys Ser Gly Lys Ser Glu Lys Ala Gln
65                  70                  75                  80

Ala Ser Ser Gly Thr Ser Thr Thr Thr Ser Val Ala Gln Ala Ser Gln
                    85                  90                  95

Thr Ala Thr Ala Gln Ala Val His Gly Ala Arg Asp Ser Gly Phe Asn
                100                 105                 110

Ser Asp Gly Ser Ala Thr Leu Pro Ser Pro Thr Gly Thr Glu Val Asn
                115                 120                 125

Gly Val Val Leu Arg Lys Gly Met Gly Thr Leu Ala Leu Met Gly Leu
                130                 135                 140

Ile Met Thr Leu Leu Ala Gln Ala Ser Ala Lys Ser Trp Ser Ser Ser
145                 150                 155                 160

Phe Gln Gln Gln Asn Gln Ala Ile Gln Asn Gln Val Ala Met Ala Pro
                165                 170                 175

Glu Ile Gly Asn Ala Ile Arg Thr Gln Ala Asn His Gln Ala Gln Ala
                180                 185                 190

Thr Glu Leu Gln Ala Gln Gln Ser Leu Ile Ser Gly Ile Thr Asn Ile
                195                 200                 205

Val Gly Phe Ala Val Ser Val Gly Gly Gly Ile Leu Ser Ala Ser Lys
                210                 215                 220

Ser Leu Gly Gly Leu Lys Ser Ala Ala Phe Thr Asn Glu Thr Ala Ser
225                 230                 235                 240

Ala Thr Thr Ser Ala Thr Ser Ser Leu Ala Lys Thr Ala Thr Ser Ala
                245                 250                 255

Leu Asp Asp Val Ala Gly Thr Ala Thr Ala Val Gly Ala Lys Ala Thr
                260                 265                 270

Ser Gly Ala Ala Ser Ala Ala Ser Ser Ala Ala Thr Lys Leu Thr Gln
                275                 280                 285

Asn Met Ala Glu Ser Ala Ser Lys Thr Leu Ser Gln Thr Ala Ser Lys
                290                 295                 300

Ser Ala Gly Gly Leu Phe Gly Gln Ala Leu Asn Thr Pro Ser Trp Ser
305                 310                 315                 320

Glu Lys Val Ser Arg Gly Met Asn Val Val Lys Thr Gln Gly Thr Arg
                325                 330                 335

Ala Ala Lys Phe Ala Gly Arg Ala Leu Ser Ser Ala Met Asn Ile Ser
                340                 345                 350

Gln Met Val His Gly Leu Thr Ala Gly Ile Asp Gly Ile Val Gly Gly
                355                 360                 365

Val Ile Gly Ala Gln Val Ala Gln Glu Gln Arg Met Ala Gly Met Ala
                370                 375                 380

Glu Ala Arg Ala Glu Glu Leu Lys Ser Leu Asn Ser Val Gln Ala Gln
385                 390                 395                 400

Tyr Ala Ser Gln Ala Gln Gln Leu Gln Glu Gln Ser Gln Gln Ser Phe
                405                 410                 415

Asn Ser Ala Leu Gln Thr Leu Gln Ser Ile Ser Asp Ser Ala Leu Gln
                420                 425                 430

Thr Thr Ala Ser Met Phe Asn
                435
```

TYPE III SECRETION INJECTISOME PROTEINS FOR TREATMENT AND PREVENTION OF CHLAMYDIAL INFECTIONS

RELATED APPLICATIONS

This application is a national phase entry of PCT/CA2015/000030 filed on Jan. 16, 2015 (which designates the U.S.) which claims the benefit of priority from U.S. Provisional Patent Application No. 61/928,117 filed on Jan. 16, 2014, the contents of which are hereby incorporated by reference in their entirety.

INCORPORATION OF SEQUENCE LISTING

A computer readable form of the Sequence Listing "3244-P47591US00_SequenceListing.txt" (20,480 bytes), submitted via EFS-WEB and created on Jul. 15, 2016, is herein incorporated by reference.

FIELD

The present disclosure relates to novel methods and compositions for treating and/or preventing chlamydial infection and disease. In particular, the disclosure relates to Type III secretion injectisome proteins for administration to subjects and for use in treating and/or preventing chlamydial infection and disease.

BACKGROUND

Epidemiology of Chlamydial Infections

*Chlamydia* is a common sexually transmitted disease caused by the bacterium *Chlamydia trachomatis* (Senior 2012). According to a WHO study an estimated 92 million chlamydial infections occurred worldwide in the year 1999, affecting more women (50 million) than men (42 million). The USA Center for Disease Control and Prevention reports *Chlamydia* as the most frequently reported infectious disease in the USA, with an estimated 4-5 million cases reported annually. Many infected individuals remain asymptomatic in the short term but may progress to chronic infection in the medium-long term with serious consequences such as infertility and Pelvic Inflammatory Disease (PID).

*Chlamydia trachomatis* infection affects approximately 3% of sexually active young adults and up to 18% of high risk populations. The great majority of those infected are under 25 years of age, and if left untreated, the infection has significant consequences for female fertility.

Most *Chlamydia* notifications are in the 15 to 24 years age group with 73% of females and 55% of males infected in this age group. Nearly 2% of females aged 15-24 years were notified with *Chlamydia* in 2006. Estimates of the current infertility rate for Western countries have shown that by the end of one year of unprotected sexual intercourse, 10-15% of couples will fail to conceive with 37% and 85% of infertility in developed and developing countries respectively due to tubal factor infertility. *C. trachomatis* has received significant attention as a primary etiological factor, responsible for significant levels of PID and salpingitis, ectopic pregnancies, tubal infertility and epididymitis in young males.

*Chlamydia* are the major cause of sexually transmitted disease, and despite all current efforts, the incidence of infection continues to increase, particularly in young adults and high risk populations. The costs of *Chlamydia* infections are several-fold. The initial costs relate to the testing and treatment of infected individuals, to ensure that transmission of the infectious agent is minimized. The second relates to the downstream disease caused by *Chlamydia* infections, which includes pelvic inflammatory disease, tubal blockage and infertility, in women. The third aspect relates to the cost of implementing improved research strategies into health policies and programs. Indeed, the various *Chlamydia* sequale are a socio economic burden resulting in a total healthcare cost, of more than US$2 billion (1994) as estimated by the Institute of Medicine. The WHO also estimates that the direct costs of caring for those with PID could be as high as US$10 billion per annum (James et al. 2008).

Trachoma, caused by *C. trachomatis* serovars A, B and C, is the leading cause of infectious blindness worldwide and despite long-standing control efforts, it is estimated that more than 500 million people still are at high risk of infection, over 140 million persons are infected and about 6 million are blind in Africa, the Middle East, Central and South-East Asia, and countries in Latin America (Global WHO Alliance for the Elimination of Blinding Trachoma by 2020).

*Chlamydia pneumoniae*, known primarily as a respiratory pathogen, was first characterized in 1989. It is the causative agent in approximately 10% of the cases of community acquired *pneumoniae* in the United States and Canada. In addition to causing pharyngitis, laryngitis, and bronchitis, it has also been associated with a number of diseases such as atherosclerosis, arthritis, multiple sclorosis, and Alzheimer's disease. The prevalence of infection with *C. pneumoniae* increases with age and it is estimated that 40-60% of adults have anti-*C. pneumoniae* IgG antibodies.

Biology of Chlamydiae

Within the family Chlamydiaceae there are 9 different species: *Chlamydia caviae, Chlamydia abortus, Chlamydia psittaci, Chlamydia felis, Chlamydia pecorum, Chlamydia suis, Chlamydia muridarum, Chlamydia trachomatis*, and *Chlamydia pneumoniae*.

The order Chlamydiales are Gram-negative, obligate, intracellular pathogens which display a broad host range across the animal kingdom including but not limited to amoebae, insects, fish, reptiles, birds, amphibians, koalas, domesticated animals, and humans (Polkinghorne et al. 2009). In the case of the koala, *Chlamydia* is the major infection and when combined with habitat loss represents a major threat to remaining populations. Multiple eukaryotic cell types may be infected by Chlamydiales including epithelial and smooth muscle cells, macrophages, dendritic cells, and various cell types of the central nervous system, but the tissue tropism of these pathogens varies based on the species. *Chlamydia* species also infect and causes disease in a range of animals including birds, sheep, cattle, cats and marsupials, including the koala (Polkinghorne et al. 2009).

Chlamydiae are obligate intracellular pathogens that require type III secretion (T3S) to invade cells and replicate intracellulary within a cytoplasmic vacuole called an inclusion body (Johnson et al. 2008; Fields and Hackstadt 2000; Stone et al. 2010; 2011; 2012; Toor et al. 2012). All members of the genus *Chlamydia* share a unique, biphasic life cycle that is initiated by attachment of the metabolically quiescent elementary body (EB) to the host cell. Once the EBs are attached to the host cell, type III secretion (T3S) is used to facilitate bacterial internalization through injection of effector proteins such as the translocated actin recruitment protein (TARP) (Clifton et al. 2004). Activation of the host MEK-ERK and PI-3 kinase pathways are also involved in Chlamydial uptake which is mediated by T3S effectors (Coombes and Mahony 2002). T3S is likely also involved in preventing phagosome endosome fusion through the secretion of unidentified effectors. The remaining intracellular portion of the life-cycle takes place within a plasma-membrane derived vacuole known as an inclusion. Once inside the inclusion, EBs transform into metabolically active reticulate bodies (RB) that becomes associated with the inclusion membrane. Interaction with the inclusion membrane allows RBs to communicate with the host cell by secretion of T3S effectors permitting *Chlamydia* to commandeer host cell pathways to acquire lipids, cholesterol, and other nutrients crucial for growth and replication. RB replication results in expansion of the inclusion body until some unknown stimulus signals the non-infectious RBs to transform into infectious EBs which exit the host cell either by cell lysis or a packaged released mechanism termed extrusion, leaving the host cell intact (Hybiske and Stephens 2007).

T3S is a virulence factor used by several Gram-negative bacteria including Chlamydiae, *Yersinia*, *Salmonella*, *Pseudomonas* and *E. coli* whereby effector proteins are transported from the bacterial cytosol into the host cell cytoplasm (Beeckman and Vanrampay 2009). The type III secretion system translocates effectors through the inner membrane, periplasmic space, and outer membrane in a single-step using a syringe-like apparatus known as an injectisome (Galan and Wolf-Watz 2006, Ghosh 2004). The injectisome is constructed of 20-25 proteins spanning the inner membrane, periplasm and outer membrane, extending into the extracellular milieu to allow for host cell sensing and contact. The apparatus is activated upon host cell-contact, possibly by interaction of the T3S injectisome with cholesterol and sphingolipid rich microdomains, termed lipid rafts, in the host cell membrane. At the tip of the T3S needle is the needle-tip complex that is crucial for sensing host-cell contact and initiating secretion (Markham et al. 2009; Stone et al. 2012). Upon host cell contact, the T3S apparatus injects two translocator proteins, YopB/D in Yersiniae and CopB/D in Chlamydiae, into the host cell membrane to form the translocon, a molecular pore through which secreted proteins can enter the host cell (Goure 2004; 2005). Insertion of hydrophobic translocator proteins into host cell membranes is thought to be dependent on lipid-rafts since in the absence of cholesterol, translocators do not form a pore and infection is inhibited. In Yersiniae, the needle-filament protein YscF extends from the bacterial outer-membrane and houses the needle-tip complex consisting of the sensor protein and possibly the translocators (Zauberman et al. 2008). The needle-tip protein of *Yersinia*, LcrV, functions in this capacity by first recognizing cell contact and also acting as an extracellular chaperone facilitating translocator insertion into the host membrane. How the needle-tip protein senses the host is unknown, however, one hypothesis is that a pre-formed tip complex consisting of LcrV (pentameric or hexameric) and the translocator protein YopB (single copy) act in concert to sense the host cell. Evidence also exists suggesting that LcrV may play an additional role inside the host cell inhibiting LPS-induced polymerization of actin and cytoskeleton rearrangement. Crystallographic analysis of LcrV revealed a dumbbell-like structure with two globular domains on either end of a "grip" formed by a conserved coiled-coil motif. In *C. trachomatis* the CT584 protein has been proposed as the needle tip protein based on comparisons of biophysical properties to other tip proteins, however, nothing is known about the structure or function of Chlamydial needle tip proteins (Markham et al. 2009). In *Chlamydia pneumonia*, Cpn0803 protein has been shown to interact with several T3S components viz. the needle filament protein, the ATPase and the multi-cargo shuttling protein CdsQ (Stone et al. 2012). X-ray crystallographic analysis of Cpn0803 has revealed a conserved N-terminal 4-helix bundle, but an overall unique fold not seen in LcrV orthologs (Stone et al. 2012). PepScan mapping and Rosetta Docking analysis predict that Cpn0803 functions on the injectisome tip as a tetramer. Collectively, these data provide strong evidence for the role of Cpn0803 as the needle-tip protein in *Chlamydia pneumoniae*. The needle tip proteins in chlamydial species are highly genetically conserved. The amino acid similarity between CT584 and Cpn0803 is 94% with 83% amino acid identity. For Cpn0803 and *C. pecorum* (G5S0239) the overall alignment score is 91% and for Cpn0803 and *C. psittaci* (G500989) the overall similarity is 86% and for *C. psittaci* and *C. pecorum* the alignment score is 84%. Alignment score reflects how well two sequences are aligned. Similarity between two sequences is then calculated using the optimal alignment.

Need for Vaccine

Genital tract infection with *Chlamydia trachomatis* is an escalating global public health concern causing considerable morbidity and socioeconomic burden worldwide. Although antibiotics are used to treat symptomatic urogenital infections, chlamydial infection remains asymptomatic in approximately 50% of infected men and 70% of infected women contributing to horizontal transmission between sexual partners. The major clinical manifestations of genital chlamydial infection in women include mucopurulent cervicitis, endometritis and pelvic inflammatory disease. Genital infection with *C. trachomatis* markedly enhances the risk for reproductive tract sequelae in women, including tubal factor infertility, chronic pain and ectopic pregnancy.

There is no commercially available vaccine for the prevention of *Chlamydia* infections in humans. Further, while vaccines have previously been developed against *C. abortus* in ruminants and swine, and against *C. felis* in cats, no vaccine currently exists for the prevention of *C. pecorum* infections in cattle, pigs or marsupials.

It is estimated that by age 30, half of all sexually active women may have been infected with *Chlamydia*. Screening for *Chlamydia* infections is usually recommended annually for all sexually active women under 26 years of age, pregnant women and older women with pre-disposing risk factors. Although antibiotic treatment is effective in the early stage of the disease, infections may reoccur and the availability and administration of a prophylactic vaccine will potentially reduce the socio-economic burden and more importantly the health consequences associated with *Chlamydia* infections.

Accordingly, a need remains for new methods to treat and/or prevent chlamydial infection and disease.

SUMMARY

The present inventors have demonstrated that administering Cpn0803 protein alone or together with CopB and/or CopD induces an immune response that is protective against a live challenge with *Chlamydia*.

Accordingly, one aspect of the disclosure provides a use of an effective amount of a protein having at least 80% sequence identity to Cpn0803, or an immunogenic fragment or epitope thereof for inducing an immune response against chlamydial infection in a subject or cell in need thereof.

In one embodiment, the use is for treating or preventing chlamydial infection in a subject or cell in need thereof.

In another embodiment, the use further comprises use of (a) a protein having at least 80% sequence identity to Cpn0809 (CopB) or an immunogenic fragment or epitope thereof or (b) a protein having at least 80% sequence identity to Cpn0808 (CopD) or an immunogenic fragment or epitope thereof.

In another embodiment, the use further comprises use of (a) a protein having at least 80% sequence identity to Cpn0809 or an immunogenic fragment or epitope thereof and (b) a protein having at least 80% sequence identity to Cpn0808 or an immunogenic fragment or epitope thereof.

In one embodiment, the protein having at least 80% sequence identity to Cpn0803 is Cpn0803 or CT584.

In another embodiment, the protein having at least 80% sequence identity to Cpn0809 is Cpn0809 or CT578.

In another embodiment, the protein having at least 80% sequence identity to Cpn0808 is Cpn0808 or CT579.

In another embodiment, the use further comprises use of an adjuvant.

In one embodiment, the adjuvant is CTA-DD, Iscomatrix, interleukin-12 (IL-12), CpG oligodeoxynucleotides, alum, Montanide ISA 720 or any combination thereof.

In another embodiment, the use further comprises use of at least one additional chlamydial protein or immunogenic fragment or epitope thereof.

In one embodiment, the additional chlamydial protein is IncA, MOMP, CopB2, CopD2, CdsF, CopN or any combination thereof.

In another embodiment, the protein having at least 80% sequence identity to Cpn0803, or an immunogenic fragment or epitope thereof is for delivery by a probiotic bacteria, optionally *Lactococcus lactis* or *Lactobacillus rhamnosus*.

In yet another embodiment, the protein having at least 80% sequence identity to Cpn0803, or an immunogenic fragment or epitope thereof is for intranasal, intravaginal, ocular or systemic administration.

Another aspect of the disclosure provides a composition comprising a protein having at least 80% sequence identity to Cpn0803 or an immunogenic fragment or epitope thereof and optionally a carrier.

In one embodiment, the composition further comprises (a) a protein having at least 80% sequence identity to Cpn0809 or an immunogenic fragment or epitope thereof or (b) a protein having at least 80% sequence identity to Cpn0808 or an immunogenic fragment or epitope thereof.

In another embodiment, the composition further comprises (a) a protein having at least 80% sequence identity to Cpn0809 or an immunogenic fragment or epitope thereof and (b) a protein having at least 80% sequence identity to Cpn0808 or an immunogenic fragment or epitope thereof.

In one embodiment, the protein having at least 80% sequence identity to Cpn0803 is Cpn0803 or CT584.

In another embodiment, the protein having at least 80% sequence identity to Cpn0809 is Cpn0809 or CT578.

In another embodiment, the protein having at least 80% sequence identity to Cpn0808 is Cpn0808 or CT579.

In another embodiment, the composition comprises an adjuvant.

In one embodiment, the adjuvant is CTA-DD, Iscomatrix, interleukin-12 (IL-12), CpG oligodeoxynucleotides, alum, Montanide ISA 720 or any combination thereof.

In another embodiment, the composition further comprises at least one additional chlamydial protein or immunogenic fragment or epitope thereof.

In one embodiment, the additional chlamydial protein is IncA, MOMP, CopB2, CopD2, CdsF, CopN or any combination thereof.

In another embodiment, the composition is formulated for delivery by a probiotic bacteria, optionally *Lactococcus lactis* or *Lactobacillus rhamnosus*.

In another embodiment, the composition is formulated for intranasal, intravaginal, ocular or systemic administration.

Another aspect of the disclosure provides a use of the composition described above for treating or preventing chlamydial infection or for inducing an immune response against chlamydial infection in a subject or cell in need thereof.

Figure 15:
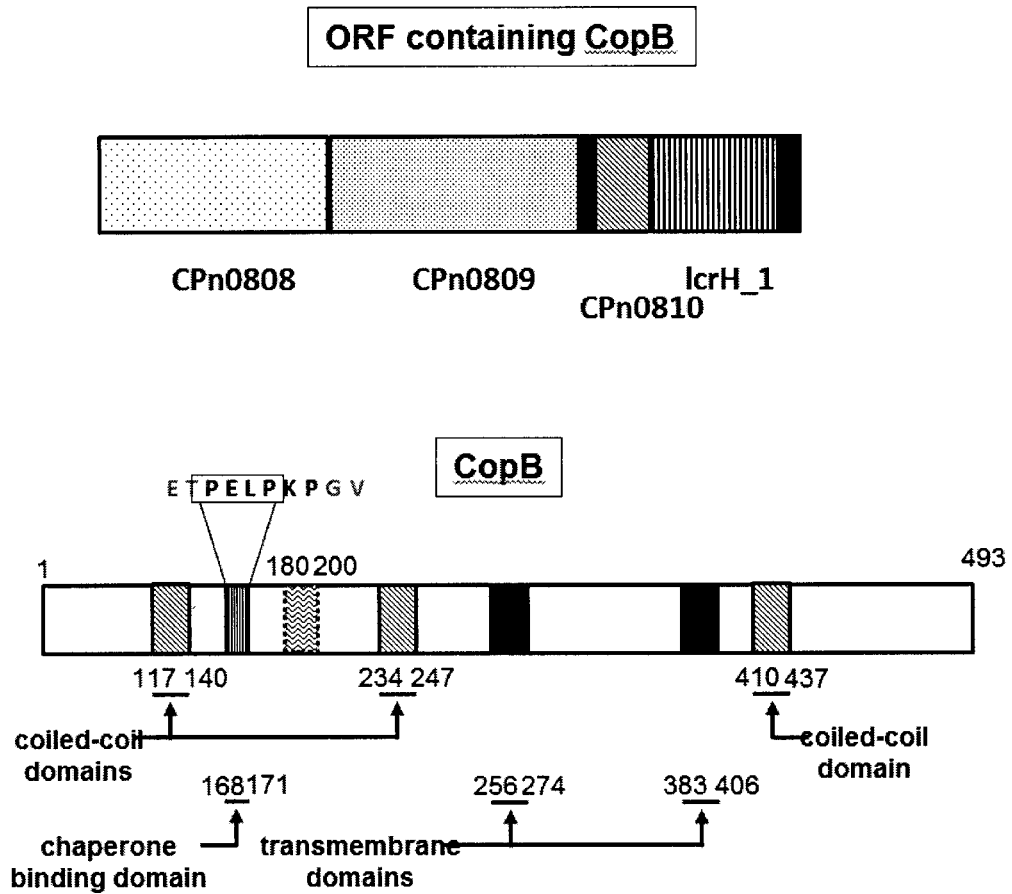

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF DRAWINGS

FIG. 1 shows the serum IgA and IgG antibody response to rMOMP and rCpn0803.

FIG. 2 shows the vaginal IgA and IgG antibody response to rMOMP and rCpn0803.

FIG. 3 shows clearance of murine *C. trachomatis* (Cmu) from the vaginal vault following intranasal (IN) immunization with CTA-1DD/CpG adjuvant (5 μg each) and live challenge with Cmu.

FIG. 4 shows the degree of genital tract pathology in mice immunized intransally (IN) with rMOMP or rCpn0803.

FIG. 5 shows clearance of murine *C. trachomatis* (Cmu) from the vaginal vault following subcutaneous (SC) immunization with Iscomatrix adjuvant (10 μg) and live challenge with Cmu.

FIG. 6 shows the degree of genital tract pathology in mice immunized subcutaneously (SC) with rMOMP or rCpn0803 and Iscomatrix adjuvant (5 μg).

FIG. 7 shows clearance of murine *C. trachomatis* (Cmu) from the vaginal vault following a combination of intranasal (IN) immunization with Iscomatrix adjuvant (5 μg) and live challenge with Cmu.

FIG. 8 shows clearance of murine *C. trachomatis* (Cmu) from the vaginal vault following a combination of subcutaneous (SC) immunization with Iscomatrix adjuvant (10 μg) and live challenge with Cmu.

FIG. 9 shows the degree of genital tract pathology in mice immunized subcutaneously (SC) with rMOMP or rCpn0803 and Isomatrix adjuvant (10 μg).

FIG. 10 shows clearance of murine *C. trachomatis* (Cmu) from the vaginal vault following live infection with Cmu in the absence of immunization.

FIG. 11 shows clearance of murine *C. trachomatis* (Cmu) from the vaginal vault in immunized and un-immunized animals (UNIMM).

FIG. 12 shows an area under the curve analysis for various immunization routes and various adjuvants, compiled data from FIGS. 3, 5, 8, and 10 compared with unimmunized animals (UNIMM).

FIG. 13 shows the degree of genital tract pathology in mice immunized subcutaneously (SC) or intranasally (IN) with either rMOMP or rCpn0803 and either CTA1-DD/CpG adjuvant or Isomatrix adjuvant or unimmunized mice (UNIMM).

FIG. 14 shows the percent inhibition of *Chlamydia* infection when pre incubated with antibodies to CopB and CopD.

FIG. 15 shows genetic organization and topographic overview of structural prediction of CopB. Solid black regions represent transmembrane domains. Diagonal stripes represent predicted coiled-coil domain in the C-terminus of the protein. Vertical stripes depict predicted Chaperone Binding Domain located from amino acids 168-171. Hydrophobic region is shown from amino acids 180-200.

Figure 16:
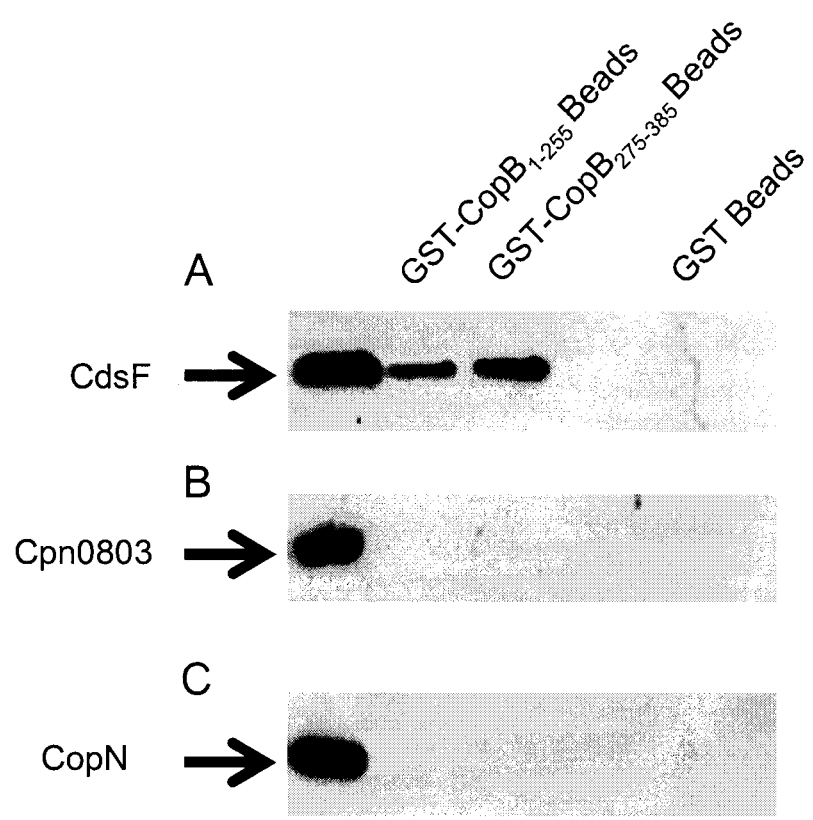

FIG. 16 shows that *Chlamydia* Outer Protein (Cop) B Interacts with T3S proteins. GST-CopB$_{1-255}$ or GST-CopD$_{407-493}$ bound to glutathione-agarose beads (bait) pulled HisMBP-CdsF (prey) out of an *E. coli* lysate in the presence of a high salt wash buffer (500 mM NaCl). Furthermore, GST-CopB fragments did not pull His-CopN or Cpn0803 out of an *E. coli* lysate in the presence of a high salt wash buffer.

Figure 17:
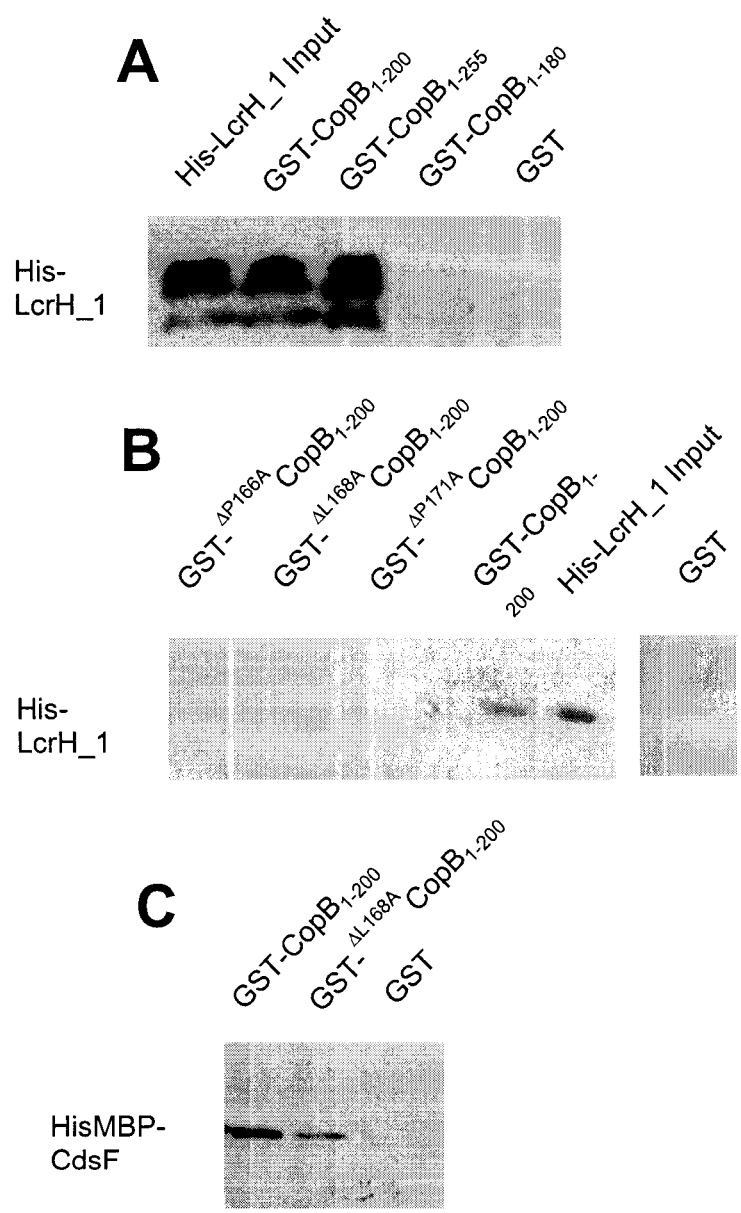

FIG. 17 shows that LcrH_1 (Cpn0811) interacts with CopB. Recombinant LcrH_1 interacted with amino acids 1-200 of CopB. CopB mutants were created using Gblock synthesis create $^{P166A}$CopB$_{1-200}$, $^{L168A}$CopB$_{1-200}$, and $^{P171A}$CopD$_{1-200}$. Mutations at the conserved amino acids within the predicted chaperone binding domain disrupted the interaction between CopB$_{1-200}$ and the chaperone LcrH_1, but not other identified interactions.

Figure 18:
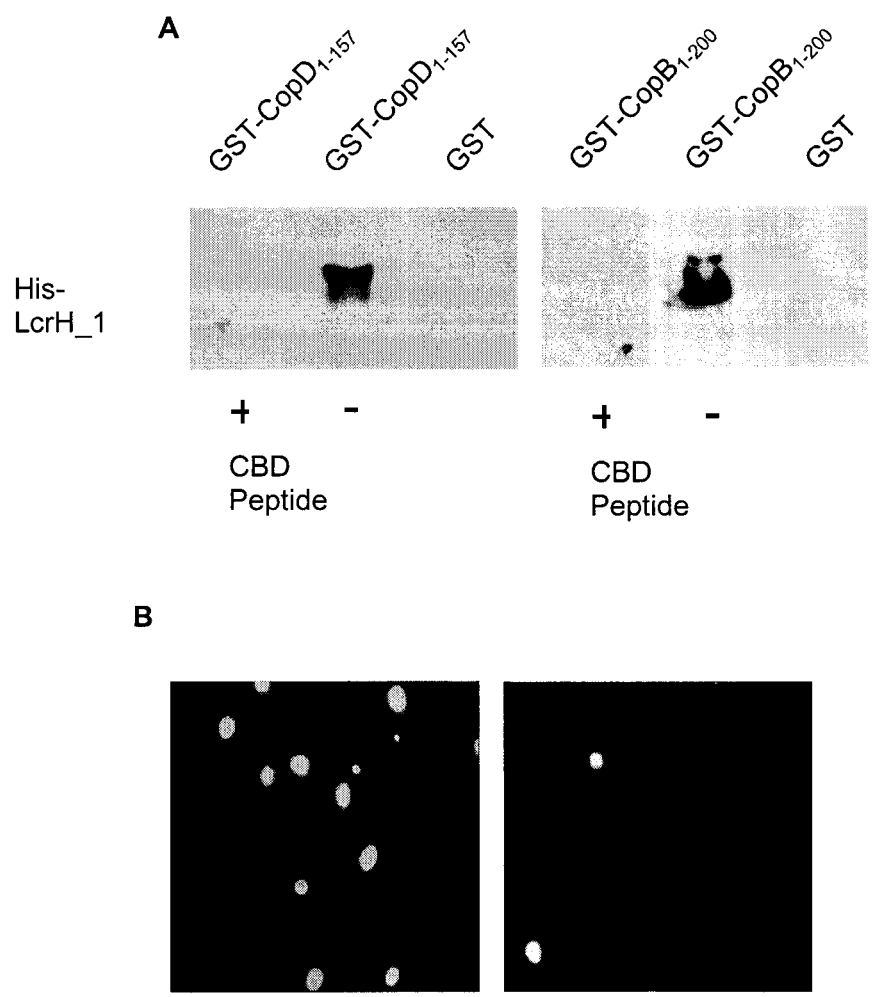

FIG. 18 shows peptide inhibition of the translocator: chaperone interaction. Panel A: Recombinant GST-CopD$_{1-157}$ or GST-CopB$_{1-200}$ was pre-incubated with 500 μM of the CBD peptide mimetic (+) or vehicle alone (−). CopD$_{1-157}$ and GST-CopB$_{1-200}$ did not interact with its putative chaperone in the presence of the CBD peptide, but did so in the absence of the peptide mimetic. Panel B: Left image is *C. pneumoniae* incubated with vehicle alone (PBS), right image is *C. pneumoniae* incubated with 500 μM CBD Peptide. Chlamydial inclusions and HeLa cells are stained.

Figure 19:
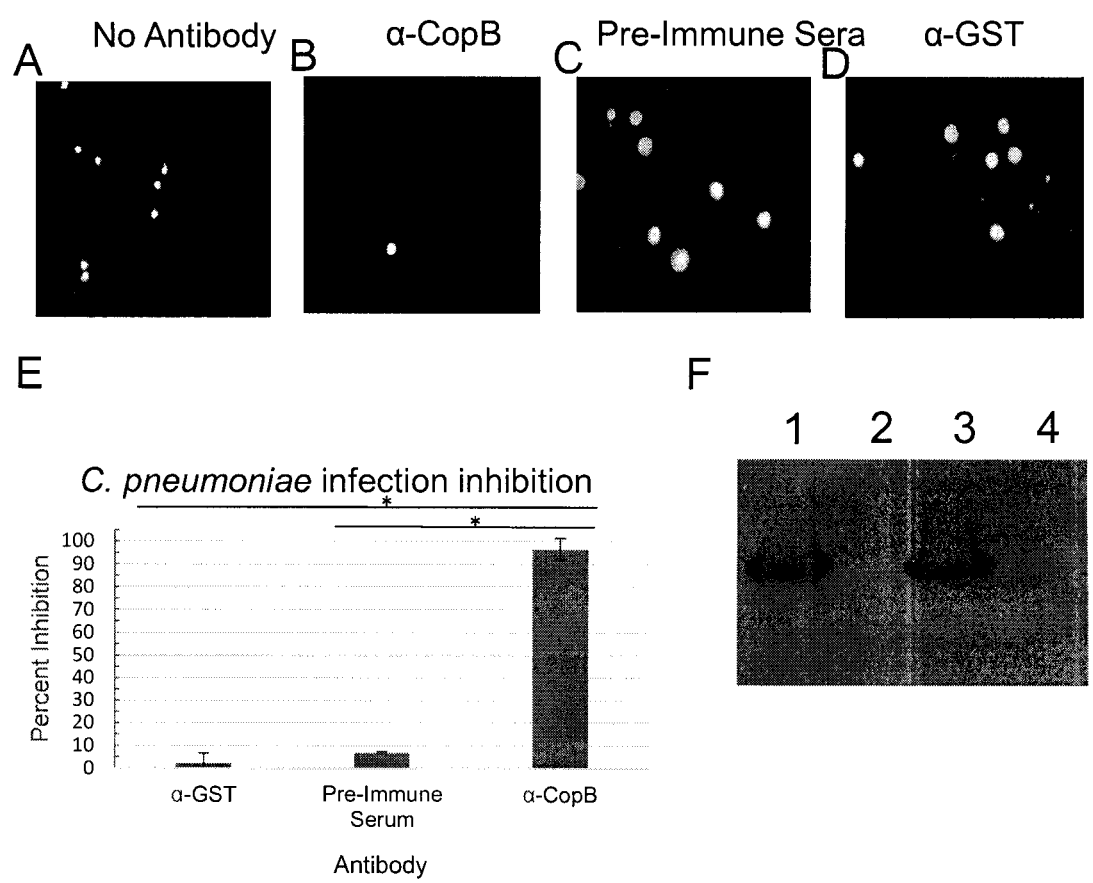

FIG. 19 shows inhibition of *Chlamydia pneumoniae* with CopB antibodies. Panels A-D show inhibition assay results performed with either no antibody (A), CopB antibody (B), pre-immune sera (C), or control antibody (α-GST) (D). Panel E shows the degree of inhibition by of CopB antibodies compared to control antibodies. Chlamydial inclusions and HeLa cells are stained. Panel F demonstrates reactivity of anti-CopB with (1) *C. pneumonia* infected HeLa cell lysate, (2) uninfected HeLa cell lysate, (3) recombinant GST-CopB$_{1-255}$ produced in *E. coli*, and (4) recombinant GST produced in *E. coli*. Experiments were performed in triplicate. Error bars represent 2 standard deviations. Images represent random fields of view. *=P<0.0001.

Figure 20:
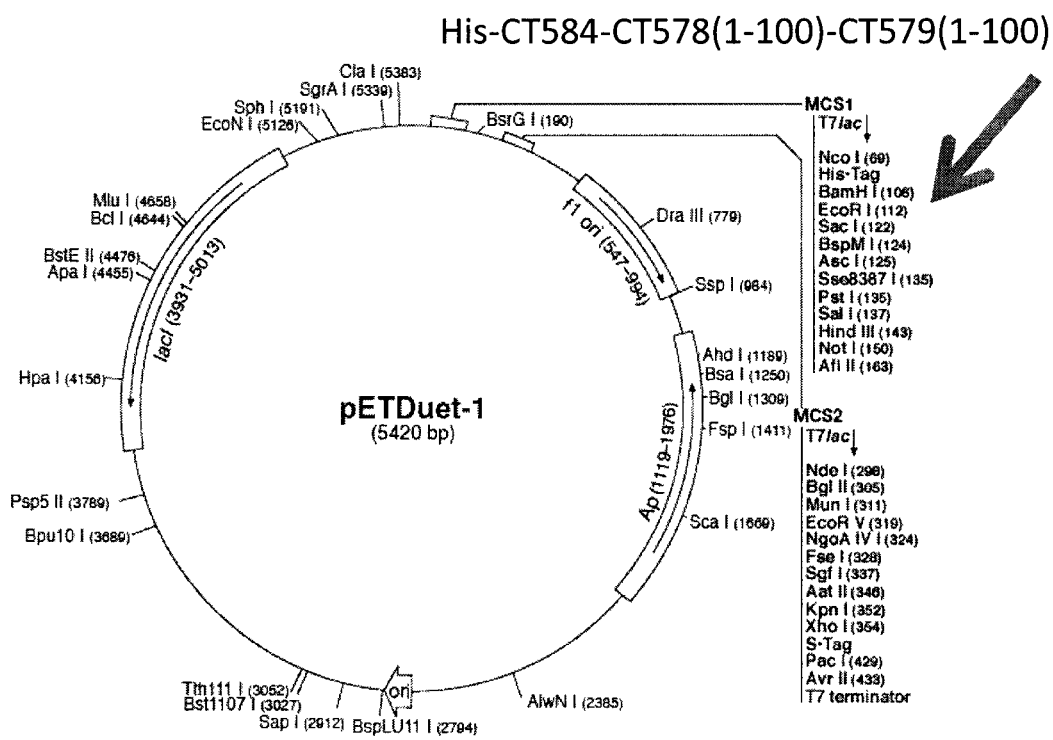

FIG. 20 shows the design of a CT584/CT578/CT579 construct. The N-terminal 100 aa of CT578 and CT579 were cloned onto the C-terminal end of CT584 since antigenicity prediction software suggested that this is an antigenic region. Furthermore, this area is hydrophilic and should create a soluble construct.

Figure 21:
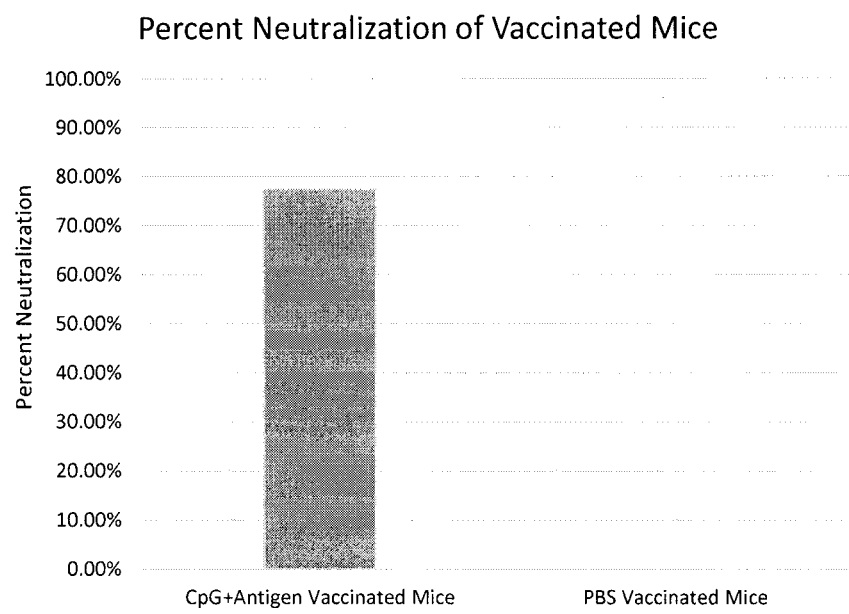

FIG. 21 shows the presence of neutralizing antibody in vaccinated mice. Serum from mice immunized with CpG+ CT584-CT578(1-100)-CT579(1-100) trivalent antigen (vaccinated group) reduced infection by 78% compared to the unvaccinated PBS control group. Each bar graph represents the mean percent reduction for the 5 mice in each group. Infection was assessed by immunofluorescence.

Figure 22:
Figure 22:

FIG. 22 shows representative urogenital tract pathology in CpG+ CT584-CT578(1-100)-CT579(1-100) trivalent antigen vaccinated mice compared to PBS vaccinated mice following *Chlamydia* infection. The pictures are representative images from two groups of five mice who were vaccinated with PBS or CpG+ trivalent antigen and then challenged with *Chlamydia trachomatis* strain *C. muridarum*. Note the presence of uterine horn and hydrosalpinx pathology in the PBS vaccinated mouse, which is reduced or almost absent in the CpG+ trivalent antigen vaccinated mouse.

DETAILED DESCRIPTION

(i) Definitions

The term "a cell" as used herein includes a a single cell as well as a plurality of cells.

The term "adjuvant" as used herein describes a substance, which can be any substance capable of being combined with the protein, peptide, fragment, epitope or composition of this disclosure to enhance, improve or otherwise modulate an immune response in a subject without deleterious effect on the subject. An adjuvant of this disclosure can be, but is not limited to, an immunostimulatory cytokine, a SYNTEX adjuvant formulation 1 (SAF-1) composed of 5 percent (wt/vol) squalene (DASF, Parsippany, N.J.), 2.5 percent Pluronic, L121 polymer (Aldrich Chemical, Milwaukee), 0.2 percent polysorbate (Tween 80, Sigma) in phosphate-buffered saline, CTA-DD, Iscomatrix, interleukin-12 (IL-12), CpG oligodeoxynucleotides, alum, Montanide ISA 720 or any combination thereof.

Suitable adjuvants also include an aluminum salt such as aluminum hydroxide gel (alum), aluminum phosphate, or algannmulin, but may also be a salt of calcium, iron or zinc, and/or may be an insoluble suspension of acylated tyrosine, or acylated sugars, cationically or anionically derivatized polysaccharides, or polyphosphazenes.

The term "chlamydial infection" as used herein refers to an infection caused by any species belonging to the bacterial family Chlamydiaceae. Chlamydiaceae are gram negative, obligate, intracellular pathogens which display a broad host range across the animal kingdom including but not limited to amoebae, insects, fish, reptiles, birds, amphibians, koalas, domesticated animals, and humans (Polkinghorne et al. 2009). In one embodiment, "chlamydial infection" refers to infection by *Chlamydia caviae, Chlamydia abortus, Chlamydia psittaci, Chlamydia felis, Chlamydia pecorum, Chlamydia suis, Chlamydia muridarum, Chlamydia trachomatis*, or *Chlamydia pneumoniae*. In one embodiment, the infection is a *Chlamydia trachomatis* infection. In another embodiment, "chlamydial infection" refers to infection by *Chlamydophila* or *Parachlamydia*. Sites of chlamydial infection include, but are not limited to, the genital, ocular and respiratory tracts.

The term "Cpn0803" as used herein refers to *Chlamydia pneumoniae* protein Cpn0803. Cpn0803 is a *Chlamydia pneumoniae* type III secretion-associated protein (Protein Accession: NP_224998.1, mRNA accession: 894751). CT584 (Protein accession: AAD18941.1, mRNA accession: 4377114) is the *Chlamydia trachomatis* homologue to Cpn0803.

The term "Cpn0809" as used herein refers to *Chlamydia pneumoniae* protein Cpn0809 (Protein accession: NP_225004, mRNA accession: 894727). Cpn0809 is also referred to as "*Chlamydia* Outer Protein B" or "CopB". CT578 (Protein accession: AAD18947) is the *Chlamydia trachomatis* homologue to Cpn0809.

The term "Cpn0808" as used herein refers to *Chlamydia pneumoniae* protein Cpn0808 (Protein accession: NP_225003). Cpn0808 is also referred to as "*Chlamydia* Outer Protein D" or "CopD". CT579 (Protein accession: AAD18946) is the *Chlamydia trachomatis* homologue to Cpn0808.

As used herein, the term "effective amount" refers to an amount of a protein, immunogen or composition of this disclosure that is sufficient to produce a desired effect, which can be a therapeutic, protective and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington, The Science And Practice of Pharmacy (20th ed. 2000)).

As used herein "effective response" or "responding effectively" means a positive or beneficial response to a particular treatment in contrast to a "lack of an effective response" which can be an ineffectual, negative or detrimental response as well as the lack of a positive or beneficial response. An effective response or lack of effective response (i.e., ineffective response) is detected by evaluation, according to known protocols, of various immune functions (e.g., cell-mediated immunity, humoral immune response, etc.) and pharmacological and biological functions as would be known in the art.

The term "epitope" as used herein refers to a molecular region on the surface of a protein or antigen capable of eliciting an immune response and of combining with the specific antibody produced by such a response.

The term "fragment" or "immunogenic fragment" as used herein refers to any portion of the proteins disclosed herein that retains immunogenic activity against *Chlamydia*. Whether or not the fragment retains immunogenic activity may be determined using techniques known in the art. A fragment of a polypeptide or protein of this disclosure can be produced by methods well known and routine in the art.

The term "homologue" as used herein relates to similar genes or proteins in different organisms due to an ancestral relationship and/or common ancestral gene sequence. In one embodiment, an amino acid sequence or protein is defined as a homologue of a polypeptide or fragment of the present disclosure if it shares significant homology to one of the polypeptides and/or fragments of the present disclosure. In one embodiment, significant homology means at least 75%, 80%, 85%, 90%, 95%, 98% and/or 100% sequence identity with another amino acid sequence.

The term "immunogen" as used herein refers to any substance capable of inducing an immune response. Examples of immunogens in the present application include, but are not limited to, Cpn0803, CopB and CopD and fragments and epitopes thereof. Other examples of immunogens include nucleic acids encoding the proteins, fragments and epitopes described herein.

The term "immune response" as used herein can refer to activation of either or both the adaptive and innate immune system cells such that they shift from a dormant resting state to a state in which they are able to elaborate molecules typical of an active immune response.

As used herein, the terms "elicit" or "induce" or "produce" (or grammatical variations thereof) in the context of an immune response against *Chlamydia* are intended to encompass the activation and/or stimulation of cells and other components of the immune system in a subject to ameliorate the effects of chlamydial infection in the subject. The immune response of this disclosure can be a protective immune response, for example, as desired in vaccination methods to treat and/or prevent infection. Protection is not required if there is some other purpose for inducing the immune response, for example, for research purposes or to produce antibody for passive immunizations or as a reagent (e.g., to detect, isolate and/or identify *Chlamydia* species).

The terms "immunogenic amount" or "effective immunizing dose," as used herein, unless otherwise indicated, mean a dose of a composition of this disclosure sufficient to induce an immune response (which can be a protective response) in the treated subject that is greater than the inherent immunity of non-immunized subjects. An immunogenic amount or effective amount or effective immunizing dose in any particular context can be routinely determined using methods known in the art.

The terms "protective immunity" or "protective immune response," as used herein, are intended to mean that the subject mounts an active immune response to the immunogenic composition and/or that the subject has been provided with passive immunity, such that upon subsequent exposure or a challenge, the animal is able to resist and/or overcome infection and/or disease. Thus, a protective immune response will decrease the incidence of morbidity and/or mortality from subsequent exposure to the chlamydial pathogens of this disclosure.

As used herein, the term "polypeptide" or "protein" is used to describe a chain of amino acids that correspond to those encoded by a nucleic acid. A polypeptide or protein of this disclosure can be a peptide, which usually describes a chain of amino acids of from two to about 30 amino acids. The term protein as used herein also describes a chain of amino acids having more than 30 amino acids and can be a fragment or domain of a protein or a full length protein. Furthermore, as used herein, the term protein can refer to a linear chain of amino acids or it can refer to a chain of amino acids that has been processed and folded into a functional protein. It is understood, however, that 30 is an arbitrary number with regard to distinguishing peptides and proteins and the terms can be used interchangeably for a chain of amino acids. The proteins of the present disclosure can be obtained by isolation and purification of the proteins from cells where they are produced naturally, by enzymatic (e.g., proteolytic) cleavage, and/or recombinantly by expression of nucleic acid encoding the proteins or fragments of this disclosure. The proteins and/or fragments of this disclosure can also be obtained by chemical synthesis or other known protocols for producing proteins and fragments.

The term "polynucleotide" and/or "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil.

The amino acid sequences of this disclosure are presented in the amino to carboxy direction, from left to right. Nucleotide sequences are presented herein, in the 5' to 3' direction, from left to right. The nucleic acids of this disclosure can be either single or double stranded (i.e., including the complementary nucleic acid). A nucleic acid of this disclosure can be the complement (e.g., complementary to the full length or only to a portion) of a nucleic acid described herein.

The term "sequence identity" as used herein refers to the percentage of sequence identity between two amino acid sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions·times·100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present application. BLAST protein searches can be performed with the XBLAST program parameters set, e.g., to score-50, wordlength=3 to obtain amino acid sequences homologous to a protein molecule of the present disclosure. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). The percent identity between two sequences can be determined using techniques similar to those described above, with or without allowing gaps. In calculating percent identity, typically only exact matches are counted.

The term "subject" as used herein includes any animal susceptible to infection by a Chlamydial species. Such a subject can be a mammal (e.g., a laboratory animal such as a rat, mouse, guinea pig, rabbit, primates, etc.), a farm or commercial animal (e.g., a cow, horse, goat, donkey, sheep, etc.), a domestic animal (e.g., cat, dog, ferret, etc.), an avian species and in particular embodiments, is a human. In another embodiment, a subject is a koala.

A "subject in need thereof" is a subject known to be, or suspected of being, infected with, or at risk of being infected with, *Chlamydia*. A subject of this disclosure can also include a subject not previously known or suspected to be infected by *Chlamydia* or in need of treatment for *Chlamydia* infection. For example, a subject of this disclosure can be administered the proteins, immunogens, or compositions of this disclosure even if it is not known or suspected that the subject is infected with *Chlamydia* (e.g., prophylactically). A subject of this disclosure is also a subject known or believed to be at risk of infection by *Chlamydia*.

The terms "treat," "treating" or "treatment" as used herein refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, prevention or delay of the onset of the disease, disorder, or illness, and/or change in clinical parameters of the condition, disorder, disease or illness, etc., as would be well known in the art. The terms "treat," "treating" or "treatment" as used herein also mean administering to a subject a therapeutically effective amount of the compositions, cells or vector constructs of the present application and may consist of a single administration, or alternatively comprise a series of applications.

As used herein, and as well understood in the art, "treatment" or "treating" is also an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment. Further any of the treatment methods or uses described herein can be formulated alone or for contemporaneous administration with other agents or therapies.

The terms "prevent," "preventing," and "prevention" and like terms are used herein to include imparting any level of prevention or protection which is of some benefit to a subject, such that there is a reduction in the incidence and/or the severity of the disease in a treated subject, regardless of whether the protection or reduction in incidence and/or severity is partial or complete.

The terms "reduce," "reduced," "reducing," and "reduction" (and grammatical variations thereof), as used herein, describe a decrease in a chlamydial infection- or disease-related parameter or symptom that is of some therapeutic value or benefit to the subject.

The terms "vaccine," "vaccination" and "immunization" are well-understood in the art, and are used interchangeably herein. For example, the terms vaccine, vaccination or immunization can be understood to be a process or composition that increases a subject's immune reaction to an immunogen (e.g., by providing an active immune response), and therefore its ability to resist, overcome and/or recover from infection (i.e., a protective immune response). In one embodiment, the term "vaccine" as used herein refers to a composition that prevents Chlamydial infection and/or treats Chlamydial infection.

(ii) Methods and Uses

The present inventors have demonstrated that administering Cpn0803 protein alone or together with CopB and/or CopD induces an immune response that is protective against a live challenge with *Chlamydia*.

Accordingly, the application discloses methods for treating or preventing chlamydial infection, comprising administering an effective amount of a protein having at least 80%, 85%, 90%, 95% or 99% sequence identity to Cpn0803, or an immunogenic fragment or epitope thereof to a subject in need thereof. Also disclosed is use of an effective amount of a protein having at least 80%, 85%, 90%, 95% or 99% sequence identity to Cpn0803, or an immunogenic fragment or epitope thereof for treating or preventing chlamydial infection in a subject in need thereof. Further disclosed is use of a protein having at least 80%, 85%, 90%, 95% or 99% sequence identity thereof to Cpn0803, or an immunogenic fragment or epitope thereof in the preparation of a medicament or vaccine for treating or preventing chlamydial infection in a subject in need thereof. Even further disclosed is a protein having at least 80%, 85%, 90%, 95% or 99% sequence identity to Cpn0803, or an immunogenic fragment or epitope thereof for use in treating or preventing chlamydial infection in a subject in need thereof.

The application also discloses methods of inducing an immune response against chlamydial infection, comprising administering an effective amount of a protein having at least 80%, 85%, 90%, 95% or 99% sequence identity to Cpn0803, or an immunogenic fragment or epitope thereof to a subject in need thereof. Also disclosed is use of an effective amount of a protein having at least 80%, 85%, 90%, 95% or 99% sequence identity to Cpn0803, or an immunogenic fragment or epitope thereof for inducing an immune response against chlamydial infection in a subject in need thereof. Further disclosed is use of a protein having at least 80%, 85%, 90%, 95% or 99% sequence identity to Cpn0803, or an immunogenic fragment or epitope thereof in the preparation of a medicament or vaccine for inducing an immune response against chlamydial infection in a subject in need thereof. Even further disclosed is a protein having at least 80%, 85%, 90%, 95% or 99% sequence identity to Cpn0803, or an immunogenic fragment or epitope thereof for use in inducing an immune response against chlamydial infection in a subject in need thereof.

In some embodiments, the immune response includes an active (e.g., a protective) immune response. In some embodiments, the immune response includes a cellular and/or humoral immune response. In other embodiments, the immune response includes a Th1 and/or Th2 immune response to provide protection.

"Treating or preventing chlamydial infection" includes alleviation or amelioration of one or more symptoms or conditions of chlamydial infection, diminishment of the extent of chlamydial infection, stabilization (i.e. not worsening) of the state of chlamydial infection, preventing spread of chlamydial infection, delay or slowing of progression chlamydial infection, amelioration or palliation of a chlamydial infection, and remission (whether partial or total), whether detectable or undetectable. In one embodiment, "treating or preventing chlamydial infection" includes reducing and/or ameliorating at least one pathological condition associated with chlamydial infection. In another embodiment, "treating or preventing chlamydial infection" includes reducing the likelihood of female genital tract pathology, including but not limited to pelvic inflammatory disease and tubal factor infertility. In another embodiment, "treating or preventing chlamydial infection" includes reducing the likelihood of infertility due to Chlamydia infection.

In addition to Cpn0803 and fragments and epitopes thereof, also contemplated for use in the present methods are proteins having at least 80%, 85%, 90%, 95% or 99% sequence identity to Cpn0803 and fragments and epitopes thereof. Examples of proteins having at least 80% sequence identity to Cpn0803 include homologues of Cpn0803 from other Chlamydia species.

In one embodiment, the protein having at least 80% sequence identity to Cpn0803 is a Cpn0803 homologue from Chlamydia caviae (hypothetical protein, accession #: WP_011006912), Chlamydia abortus (hypothetical protein, accession #: WP_006344529), Chlamydia psittaci (hypothetical protein, accession #: WP_014945399.1), Chlamydia felis (hypothetical protein, accession #: WP_011457611), Chlamydia pecorum (hypothetical protein, accession #: WP_013712331), Chlamydia suis (hypothetical protein, accession #: WP_035407010.1), Chlamydia muridarum (hypothetical protein, accession #: WP_010231811.1) or Chlamydia trachomatis (CT584, accession #: AAD18941.1).

In another embodiment, the protein having at least 80% sequence identity to Cpn0803 is CT584. CT584 is a Chlamydia trachomatis homologue to Cpn0803.

The present inventors have shown that administering Cpn0803 protein together with CopB and/or CopD induces an immune response that is protective against a live challenge with Chlamydia. Accordingly, in one embodiment, a protein having at least 80% sequence identity to Cpn0803 or an immunogenic fragment or epitope thereof is administered with (ii) (a) a protein having at least 80% sequence identity to Cpn0809 (CopB) or an immunogenic fragment or epitope thereof and/or (b) a protein having at least 80% sequence identity to Cpn0808 (CopD) or an immunogenic fragment or epitope thereof for treating and/or preventing chlamydial infection and/or for inducing an immune response to chlamydial infection.

Also contemplated for use in the present methods are proteins having at least 80%, 85%, 90%, 95% or 99% sequence identity to CopB or CopD. Examples of proteins having at least 80% sequence identity to CopB or CopD are CopB or CopD homologues from other Chlamydia species. In one embodiment, the protein having at least 80% sequence identity to CopB is a CopB homologue from Chlamydia caviae, Chlamydia abortus, Chlamydia psittaci, Chlamydia felis, Chlamydia pecorum, Chlamydia suis, Chlamydia muridarum or Chlamydia trachomatis. In one embodiment, the protein having at least 80% sequence identity to CopD is a CopD homologue from Chlamydia caviae, Chlamydia abortus, Chlamydia psittaci, Chlamydia felis, Chlamydia pecorum, Chlamydia suis, Chlamydia muridarum or Chlamydia trachomatis.

In one embodiment, the protein having at least 80% sequence identity to CopB is CT578. CT578 is a Chlamydia trachomatis homologue to CopB.

In another embodiment, the protein having at least 80% sequence identity to CopD is CT579. CT579 is a Chlamydia trachomatis homologue to CopD.

Cpn0803/CT584 or an immunogenic fragment or epitope thereof may be administered before, after and/or concurrent with the administration with CopB/CT578 or an immunogenic fragment or epitope thereof and/or CopD/CT579 or an immunogenic fragment or epitope thereof. In one embodiment, and as described in more detail below, Cpn0803/CT584 or an immunogenic fragment or epitope thereof is administered in a composition with CopB/CT578 or an immunogenic fragment or epitope thereof and/or CopD/CT579 or an immunogenic fragment or epitope thereof.

In one embodiment, Cpn0803/CT584 or an immunogenic fragment or epitope thereof is fused to CopB/CT578 or an immunogenic fragment or epitope thereof and/or CopD/CT579 or an immunogenic fragment or epitope thereof and the resulting fusion protein is administered to a subject in need thereof. Methods of producing fusion proteins are well known in the art. In one embodiment, a construct encoding a fusion protein is cloned into an expression vector for expression in E. coli. An example of a fusion protein useful in the methods described herein is 6×His-His-CT584-CT578(1-100)-CT579(1-100), where the N-terminal 100 amino acids of CT578 and CT579 are cloned onto the C-terminal end of CT584.

The following table sets out the amino acid sequences corresponding to the proteins described herein:

TABLE 1

Sequence Listings

| Protein | Organism | Sequence |
|---|---|---|
| Cpn0803 | Chlamydia pneumoniae | SEQ ID NO: 1 |
| Cpn0809/CopB | Chlamydia pneumoniae | SEQ ID NO: 2 |
| Cpn0808/CopD | Chlamydia pneumoniae | SEQ ID NO: 3 |
| CT584 | Chlamydia trachomatis | SEQ ID NO: 4 |
| CT578 | Chlamydia trachomatis | SEQ ID NO: 5 |
| CT579 | Chlamydia trachomatis | SEQ ID NO: 6 |

Further contemplated for use in the present methods are immunogenic fragments and epitopes of the proteins described herein.

As set forth herein, the term "immunogenic fragment" means a fragment (e.g., a peptide) of a protein that can stimulate either humoral or cellular immune responses in the subject. An immunogenic fragment of this disclosure can comprise, consist essentially of and/or consist of one, two, three, four or more epitopes of a protein of this disclosure. An immunogenic fragment can be any fragment of contiguous amino acids of the described proteins (for example, Cpn0803 (or CT584), CopB (or CT578) or CopD (or CT579)) protein and can be at least 5, 10, 15, 20, 25, 30, 35, 40, 45, 50, 75, 100, 150, 200, 250, 300, 350, 400, 450, 500 or 550 amino acids in length. Identification of any such immunogenic fragments is routine in the art.

In further embodiments, Cpn0803 or fragments or epitopes thereof may be administered in conjunction with additional Chlamydia proteins or fragments or epitopes thereof. Other Chlamydia proteins contemplated for use in the present methods include, but are not limited to, Chlamydia trachomatis proteins. Examples of Chlamydia trachomatis proteins include major outer membrane protein (rMOMP) and inclusion membrane protein A (rincA), etc., as are known in the art. Other examples include, but are not limited to, PorB (Ifere et al., J. Microbiol. Immunol. Infect. 40:188-200 (2007))), enolase (Finco et al. Vaccine 23:1178-1188 (2005)), Cta1 (Roan et al. PNAS 103:12069-74 (2006)), CH089 (CopN), CT147 (EEA homology), CT226 (Inc), CT442 (15 kDa Crp), CT443 (60 kDa CRP, OmcB), CT529 (Inc, CapA), CT694 (HP, IB), CT795 (HP, IB), CT806CT812 (pmpD), CT813 (Inc), CT823, CT841, pCT03, CT110 (HSP60), CT806, CT823, CT841, pCTO3 and CT813. Other Chlamydia proteins contemplated for use in the present methods include homologues of CT806, CT823, CT841, pCTO3 or CT813 protein from various Chlamydia species as well as TroA, TroB, IncA, IncB and IncC (see, e.g., U.S. Pat. No. 6,746,676 to Rockey et al. and U.S. Patent Application Publication No. 2006/0034871 to Grandi et al., each of which is incorporated by reference herein), as well as any combination thereof.

The proteins, fragments and epitopes described herein may be administered as proteins, polypeptides or peptides. In another embodiment, a nucleic acid encoding the proteins, fragments and epitopes described herein can be introduced into a subject, wherein the nucleic acid is expressed and the encoded product is produced to treat or prevent Chlamydial infection and/or elicit an immune response in the subject.

In embodiments of this disclosure wherein one or more nucleic acids are administered to a subject, the nucleic acid(s) can be present as naked nucleic acid and/or in a vector or plasmid that carries the nucleic acid(s). The nucleic acid(s) and/or vectors and/or plasmids can also be in a cell (e.g., an isolated cell) that is administered to a subject.

In certain embodiments, the proteins, fragments and/or epitopes of this disclosure can be fused with a "carrier" protein or peptide to produce a fusion protein. For example, the carrier protein or peptide can be fused to a protein and/or fragment of this disclosure to increase the stability thereof (e.g., decrease the turnover rate) in the cell and/or subject. Exemplary carrier proteins include, but are not limited to, glutathione-S-transferase or maltose-binding protein or human serum albumin. The carrier protein or peptide can alternatively be a reporter protein. For example, the fusion protein can comprise a polypeptide and/or fragment of this disclosure and a reporter protein or peptide (e.g., green fluorescent protein (GFP), β-glucoronidase, β-galactosidase, luciferase, and the like) for easy detection. As a further alternative, the fusion protein attached to the polypeptides and/or fragments and a carrier protein or peptide can be targeted to a subcellular compartment of interest, i.e., to affect the co-localization of the polypeptide and/or fragment. Any suitable carrier protein as is well known in the art can be used to produce a fusion protein of this disclosure.

The present disclosure further includes isolated polypeptides, peptides, proteins and/or fragments that are substantially equivalent to those described for this disclosure. As used herein, "substantially equivalent" can refer both to nucleic acid and amino acid sequences, for example a mutant sequence, that varies from a reference sequence by one or more substitutions (e.g., substitution with conservative amino acids as are well known in the art), deletions and/or additions, the net effect of which does not result in an undesirable adverse functional dissimilarity between reference and subject sequences. In some embodiments, this disclosure can include substantially equivalent sequences that have an adverse functional dissimilarity. For purposes of the present disclosure, sequences having equivalent biological activity and equivalent expression characteristics are considered substantially equivalent.

A protein or immunogenic fragment and/or epitope thereof of this disclosure may be from Chlamydia caviae, Chlamydia abortus, Chlamydia psittaci, Chlamydia felis, Chlamydia pecorum, Chlamydia suis, Chlamydia muridarum and/or Chlamydia trachomatis in any combination. Further, they may be from any species of Chlamydia, Chlamydophila and/or Parachlamdyia.

The proteins, immunogens and/or compositions of this disclosure can be modified according to methods known in the art and/or administered with an adjuvant in order to increase antigenicity. Methods of increasing the antigenicity of a protein or peptide are well known in the art and include, but are not limited to coupling the antigen with a heterologous protein (such as globulin or β-galactosidase or human albumin) or through the inclusion of one or more adjuvants in addition to the immunogen of this disclosure. The adjuvant can be administered with the immunogen, before administration of the immunogen, after administration of the immunogen, or any combination thereof.

An adjuvant of this disclosure, such as, for example, an immunostimulatory cytokine, can be administered before, concurrent with, and/or within a few hours, several hours of an immunogenic chlamydial composition of this disclosure to a subject.

Furthermore, any combination of adjuvants, such as immunostimulatory cytokines, can be co-administered to the subject before, after and/or concurrent with the administration of the proteins, immunogens and/or compositions of this disclosure.

The proteins, immunogens and/or compositions of this disclosure may be administered in any combination and in any ratio. It is contemplated that the above-described proteins, immunogens and/or compositions can be administered to a subject or to a cell of a subject to impart a therapeutic benefit, such as eliciting an immune response. Thus, as noted above, the present disclosure provides a method of inducing, eliciting or producing an immune response in a subject, comprising administering to the subject or to a cell of the subject an effective amount of a polypeptide and/or immunogenic fragment and/or epitope of this disclosure and/or a nucleic acid comprising a nucleotide sequence encoding a polypeptide and/or immunogenic fragment and/or epitope of this disclosure, with or without an adjuvant of this disclosure. The cell of the subject can be in vivo or ex vivo and can be, but is not limited to a CD8+ T lymphocyte (e.g., a cytotoxic T lymphocyte), an MHC I-expressing antigen presenting cell, such as a dendritic cell, a macrophage and/or a monocyte. The cell can also be an antigen presenting cell or other class I MHC-expressing cell which can be contacted with the nucleic acids and/or vectors of this disclosure under conditions whereby the nucleic acid or vector is introduced into the cell by standard methods for uptake of nucleic acid and vectors. The nucleic acid encoding the polypeptide and/or fragment of this disclosure is then expressed and the polypeptide and/or fragment product is processed within the antigen presenting cell or other MHC I-expressing cell and presented on the cell surface as an MHC I/antigen complex. The antigen presenting cell or other class I MHC-expressing cell is then contacted with an immune cell of the subject which binds the class I MHC/antigen complex and elicits an immune response which treats or prevents *Chlamydia* infection in the subject.

The proteins, immunogens and/or compositions described herein can be administered to "prime" a subject. By "prime," "primed" or "priming" (and grammatical variations thereof) as used herein, it is meant to initiate an active immune response that is less than protective until a second dose (booster) is given at a later time.

In another embodiment, the proteins, immunogens and/or compositions described herein can be administered as a "booster". "Boost" or "booster" means a second immunization, after an initial (or "priming") immunization that enhances the immune response of the subject. Therefore, in some embodiments, the disclosure provides proteins, immunogens and/or compositions that produce an anamnestic response against a *Chlamydia* infection, in a sensitized subject, comprising an anamnestic response-inducing amount of a *Chlamydia* protein immunizing component. As used herein, the term "anamnestic response" means a secondary (booster) immune response in a sensitized subject. By "sensitized subject" is meant a subject that has previously been in contact with a chlamydial antigen or antigens, either by natural exposure or by vaccination (primary immunization) with *Chlamydia* protein immunizing components.

In an additional embodiment, the present disclosure provides a method of providing passive immunity against chlamydial infection to a subject, comprising administering to the subject an effective amount of an antibody that specifically binds a protein, fragment or epitope described herein.

Detection of an immune response in the subject and/or in the cells of the subject can be carried out according to methods standard in the art for detecting a humoral and/or cellular immune response.

The proteins, immunogens and/or compositions described herein may be administered to, or used in, living organisms including humans, and animals. The term "subject" or "animal" as used herein refers to any member of the animal kingdom, in one embodiment a mammal such as a human being. In another embodiment, the subject is a koala.

An example of treatment of a standard patient would include an intranasal, intramuscular, intradermal, or intraperitoneal administration of the proteins, immunogens and/or compositions described herein, and optionally an adjuvant, given at various times following infection and then monitoring clinical improvement. Other methods of administration include, but are not limited to, oral, rectal, topical, inhalation (e.g., via an aerosol), buccal (e.g., sub-lingual), vaginal (e.g., vaginal ring), intraurethral, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces), ocular and transdermal administration. The proteins, immunogens and/or compositions can also be administered via a skin scarification method, transdermally via a patch, liquid or gel or subdermally such that the proteins, immunogens and/or compositions are released over time. In another embodiment, the proteins, immunogens and/or compositions are administered via a probiotic bacteria, optionally *Lactococcus lactis* or *Lactobacillus rhamnosus*. The most suitable route in any given case will depend, as is well known in the art, on such factors as the species, age, gender and overall condition of the subject, the nature and severity of the infection being treated or prevented and/or on the nature of the particular composition (i.e., dosage, formulation) that is being administered.

The frequency of administration of the proteins, immunogens and/or compositions of this disclosure can be as frequent as necessary to impart the desired therapeutic or protective effect. For example, the proteins, immunogens and/or compositions can be administered one, two, three, four or more times per day, one, two, three, four or more times a week, one, two, three, four or more times a month, one, two, three or four times a year or as necessary to control the condition. In some embodiments, one, two, three or four doses over the lifetime of a subject can be adequate to achieve the desired therapeutic or protective effect. In some embodiments, alternate day dosing can be employed (e.g., every other day). The amount and frequency of administration of the proteins, immunogens and/or compositions of this disclosure will vary depending on the particular condition being treated or to be prevented and the desired therapeutic or protective effect.

In some embodiments, an effective immunizing dose or immunogenic amount or effective amount can comprise one or more (e.g., two or three or four or more) doses of the proteins, immunogens and/or compositions of this disclosure at any time interval (e.g., hourly, daily, weekly, monthly, yearly, etc.) so as to achieve and/or maintain the desired level of protection and/or other therapeutic benefit.

The efficacy of treating or preventing *Chlamydia* infection by the methods of the present disclosure can be determined by detecting a clinical improvement as indicated by a change in the subject's symptoms and/or clinical parameters, as would be well known to one of skill in the art.

(iii) Compositions

The immunogens (proteins, fragments, epitopes and nucleic acids) described herein may be formulated into pharmaceutical compositions or vaccines for administration to subjects and/or use in subjects in a form suitable for administration in vivo.

Accordingly, in one embodiment, the disclosure provides a composition comprising, consisting essentially of or consisting of a protein having at least 80%, 85%, 90%, 95% or 99% sequence identity to Cpn0803 or an immunogenic fragment or epitope thereof. In another embodiment, the disclosure provides a composition comprising, consisting essentially of or consisting of a nucleic acid encoding a protein having at least 80%, 85%, 90%, 95% or 99% sequence identity to Cpn0803 or an immunogenic fragment or epitope thereof.

In another embodiment, the disclosure provides a composition comprising, consisting essentially of or consisting of a protein having at least 80%, 85%, 90%, 95% or 99% sequence identity to Cpn0803 or an immunogenic fragment or epitope thereof and (a) a protein having at least 80%, 85%, 90%, 95% or 99% sequence identity to Cpn0809 or an immunogenic fragment or epitope thereof and/or (b) a protein having at least 80%, 85%, 90%, 95% or 99% sequence identity to Cpn0808 or an immunogenic fragment or epitope thereof. In another embodiment, the disclosure provides a composition comprising, consisting essentially of or consisting of a nucleic acid encoding protein having at least 80%, 85%, 90%, 95% or 99% sequence identity to Cpn0803 or an immunogenic fragment or epitope thereof and (a) a nucleic acid encoding a protein having at least 80%, 85%, 90%, 95% or 99% sequence identity to Cpn0809 or an immunogenic fragment or epitope thereof and/or (b) a nucleic acid encoding a protein having at least 80%, 85%, 90%, 95% or 99% sequence identity to Cpn0808 or an immunogenic fragment or epitope thereof.

The compositions optionally include an adjuvant, namely a substance capable of being combined with the protein, peptide, fragment, epitopes of this disclosure to enhance, improve or otherwise modulate an immune response in a subject without deleterious effect on the subject. Examples of adjuvants include, but is not limited to, an immunostimulatory cytokine, a SYNTEX adjuvant formulation 1 (SAF-1) composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Other possible adjuvants include CTA-DD, Iscomatrix, interleukin-12 (IL-12), CpG oligodeoxynucleotides, alum, Montanide ISA 720 or any combination thereof. Suitable adjuvants also include an aluminum salt such as aluminum hydroxide gel (alum), aluminum phosphate, or algannmulin, but may also be a salt of calcium, iron or zinc, and/or may be an insoluble suspension of acylated tyrosine, or acylated sugars, cationically or anionically derivatized polysaccharides, or polyphosphazenes.

The compositions described herein can be prepared by per se known methods for the preparation of pharmaceutically acceptable compositions that can be administered to subjects, such that an effective quantity of the immunogen is combined in a mixture with a pharmaceutically acceptable carrier. Suitable carriers are described, for example, in Remington's Pharmaceutical Sciences (Remington's Pharmaceutical Sciences, 20$^{th}$ ed., Mack Publishing Company, Easton, Pa., USA, 2000). On this basis, the compositions include, albeit not exclusively, solutions of the substances in association with one or more pharmaceutically acceptable carriers or diluents, and contained in buffered solutions with a suitable pH and iso-osmotic with the physiological fluids.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1 (2,3-dioleyloxy)propyl)N,N,N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the patient.

Pharmaceutical compositions may also include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. Proteins may be supplied, for example but not by way of limitation, as a lyophilized powder which is reconstituted with sterile water or saline prior to administration to the patient.

The compositions may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

It is further contemplated that the present disclosure provides a kit comprising the compositions of this disclosure. It would be well understood by one of ordinary skill in the art that the kit of this disclosure can comprise one or more containers and/or receptacles to hold the reagents (e.g., antibodies, antigens, nucleic acids) of the kit, along with appropriate buffers and/or diluents and/or other solutions and directions for using the kit, as would be well known in the art. Such kits can further comprise adjuvants and/or other immunostimulatory or immunomodulating agents, as are well known in the art.

The compositions and kits of the present disclosure can also include other medicinal agents, pharmaceutical agents, carriers, diluents, immunostimulatory cytokines, etc. Actual methods of preparing such dosage forms are known, or will be apparent, to those skilled in this art.

As noted above, the compositions of this disclosure can be administered to a cell of a subject or to a subject either in vivo or ex vivo. For administration to a cell of the subject in vivo, as well as for administration to the subject, the compositions of this disclosure can be administered orally, intranasally, intravaginally, intraocularly, parenterally (e.g., intravenously), by intramuscular injection, by intraperitoneal injection, subcutaneous injection, transdermally, extracorporeally, topically or the like. Also, the compositions of this disclosure can be pulsed onto dendritic cells, which are isolated or grown from a subject's cells, according to methods well known in the art, or onto bulk peripheral blood mononuclear cells (PBMC) or various cell subfractions thereof from a subject.

In one embodiment, the compositions of this disclosure are formulated for delivery by a probiotic bacteria, optionally *Lactococcus lactis* or *Lactobacillus rhamnosus*.

The exact amount(s) of the composition(s) of this disclosure that will be required will vary from subject to subject, depending on the species, age, weight and general condition of the subject, the particular composition used, its mode of administration and the like. Thus, it is not possible to specify an exact amount for every composition of this disclosure. However, effective amount can be determined by one of ordinary skill in the art using only routine experimentation given the teachings herein and that are well known in the art.

The pharmaceutical compositions of this disclosure include those suitable for oral, intranasal, rectal, topical, inhalation (e.g., via an aerosol) buccal (e.g., sub-lingual), vaginal (e.g., vaginal ring), intraurethral, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces), ocular and transdermal administration. The compositions herein can also be formulated for administered via a skin scarification method or transdermally via a patch, liquid or gel. The compositions can also be formulated for delivery subdermally in the form of a biodegradable material that releases the compositions over time. The most suitable route in any given case will depend, as is well known in the art, on such factors as the species, age, gender and overall condition of the subject, the nature and severity of the infection being treated or prevented and/or on the nature of the particular composition (i.e., dosage, formulation) that is being administered.

As described above, the frequency of administration of a composition of this disclosure can be as frequent as necessary to impart the desired therapeutic or protective effect. The amount and frequency of administration of the composition of this disclosure will vary depending on the particular condition being treated or to be prevented and the desired therapeutic or protective effect.

In some embodiments, an effective immunizing dose or immunogenic amount or effective amount can comprise one or more (e.g., two or three or four or more) doses of the compositions of this disclosure at any time interval (e.g., hourly, daily, weekly, monthly, yearly, etc.) so as to achieve and/or maintain the desired level of protection and/or other therapeutic benefit.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present application.

EXAMPLES

Example 1. Cpn0803 Induces an Immune Response that is Protective Against a Live Challenge with *Chlamydia*

Serum IgA and IgG Antibody Response to rCpn0803 (FIG. 1)

Mice were either immunized intranasally (IN) or subcutaneously (SC) with either CTA1-DD/CpG 1826 adjuvant (5 ug each) or Iscomatrix adjuvant (5 ug IN or 10 ug SC) on days 0, 7, 14 and boosted on day 28. Five Female BALB/c mice were used in each group. Blood samples were collected on day 35 and vaginal washes collected daily for 4 days from days 32-35. IgG and IgA levels were measured by ELISA and titers expressed as the reciprocal of the end point dilution.

Figure 2:
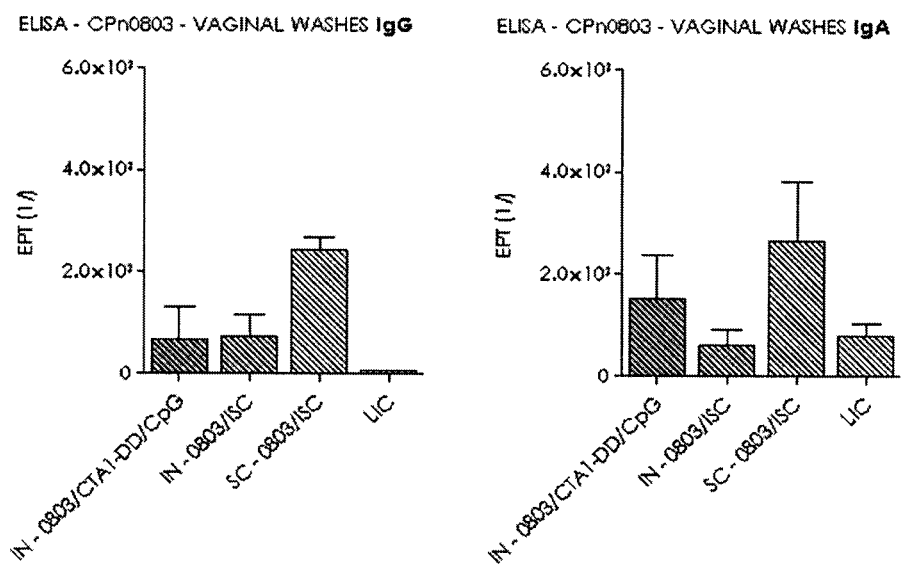

Vaginal IgA and IgG Antibody Response to rCpn0803 (FIG. 2)

Mice were either immunized intranasally (IN) or subcutaneously (SC) on days 0, 7, 14 and boosted on day 28. Five Female BALB/c mice were used in each group. Vaginal washes collected daily for 4 days from days 32-35. IgG and IgA levels were measured by ELISA and titers expressed as the reciprocal of the end point dilution.

Figure 3:
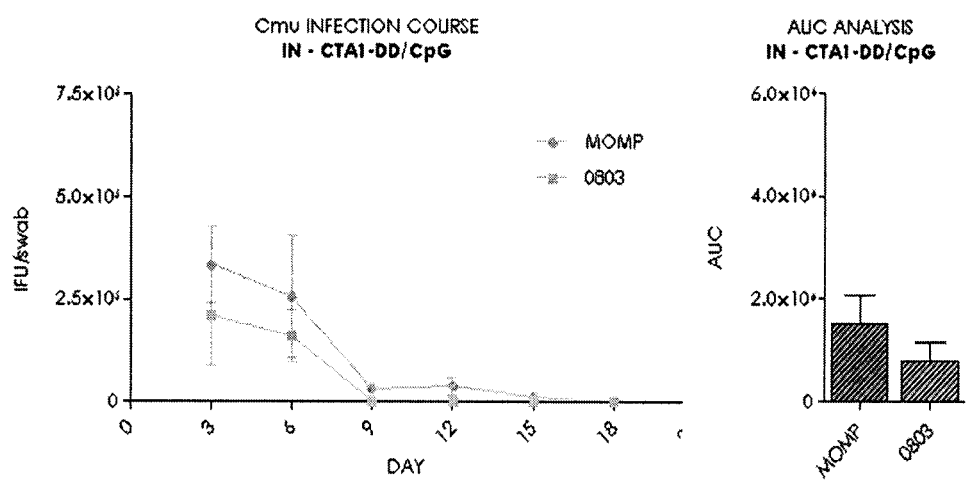

Clearance of Murine *C. trachomatis* (Cmu) from the Vaginal Vault Following Intranasal (IN) Immunization with CTA-1DD/CpG Adjuvant (5 ug Each) and Live Challenge with Cmu (FIG. 3)

Mice were immunized with either rMOMP or rCpn0803 as described in FIG. 1, then challenged with $5 \times 10^4$ IFU Cmu intravaginally on day 42. Vaginal swabs were collected every 3 days for 21 days to assess the level of Cmu infection in McCoy cells and expressed as IFU/swab (left panel). The area under the curve (AUC) analysis (right panel) allows comparison of extent of infection by combining the intensity and duration of Cmu infection between groups.

Figure 4:
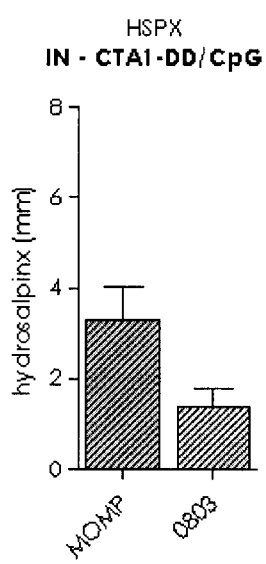

Degree of Genital Tract Pathology in Mice Immunized Intransally (IN) with rMOMP or rCpn0803 (FIG. 4)

Mice were immunized as described in FIG. 1, challenged with live Cmu, and oviducts were removed 35 days after challenge and assessed for the presence of hydrosalpinx (hspx) which was measured in mm if present.

Figure 5:
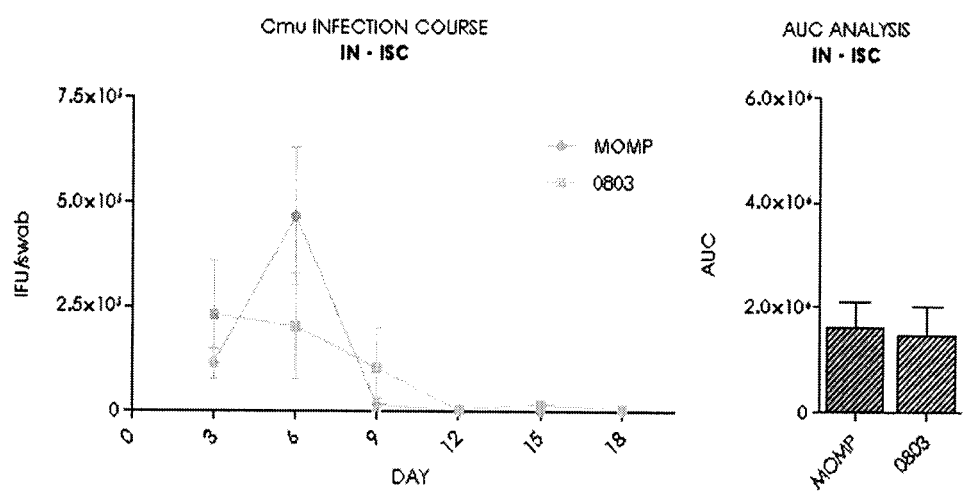

Clearance of Murine *C. trachomatis* (Cmu) from the Vaginal Vault Following Subcutaneous (SC) Immunization with Iscomatrix Adjuvant (10 µg) and Live Challenge with Cmu (FIG. 5)

Mice were immunized with either rMOMP or rCpn0803 as described in FIG. 1, then challenged with $5 \times 10^4$ IFU Cmu intravaginally on day 42. Vaginal swabs were collected every 3 days for 21 days to assess the level of Cmu infection in McCoy cells and expressed as IFU/swab (left panel). The area under the curve (AUC) analysis (right panel) allows comparison of extent of infection by combining the intensity and duration of Cmu infection between groups.

Figure 6:
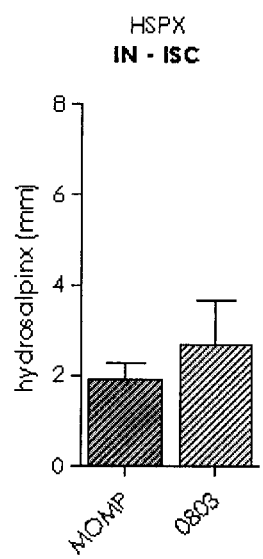

Degree of Genital Tract Pathology in Mice Immunized Subcutaneously (SC) with rMOMP or rCpn0803 and Iscomatrix Adjuvant (5 µg) (FIG. 6)

Figure 7:
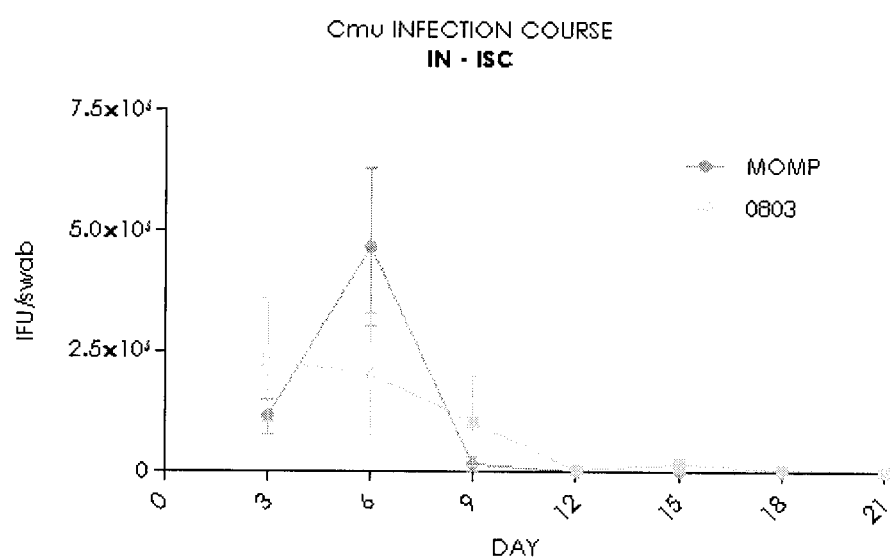

Mice were immunized as described in FIG. 1, challenged with live Cmu, and oviducts were removed 35 days after challenge and assessed for the presence of hydrosalpinx (hspx) which was measured in mm if present Clearance of Murine *C. trachomatis* (Cmu) from the Vaginal Vault Following a Combination of Intranasal (IN) Immunization with Iscomatrix Adjuvant (5 ug) and Live Challenge with Cmu (FIG. 7)

Mice were immunized with either rMOMP or rCpn0803 as described in FIG. 1, then challenged with $5 \times 10^4$ IFU Cmu intravaginally on day 42. Vaginal swabs were collected every 3 days for 21 days to assess the level of Cmu infection in McCoy cells and expressed as IFU/swab (left panel).

Figure 8:
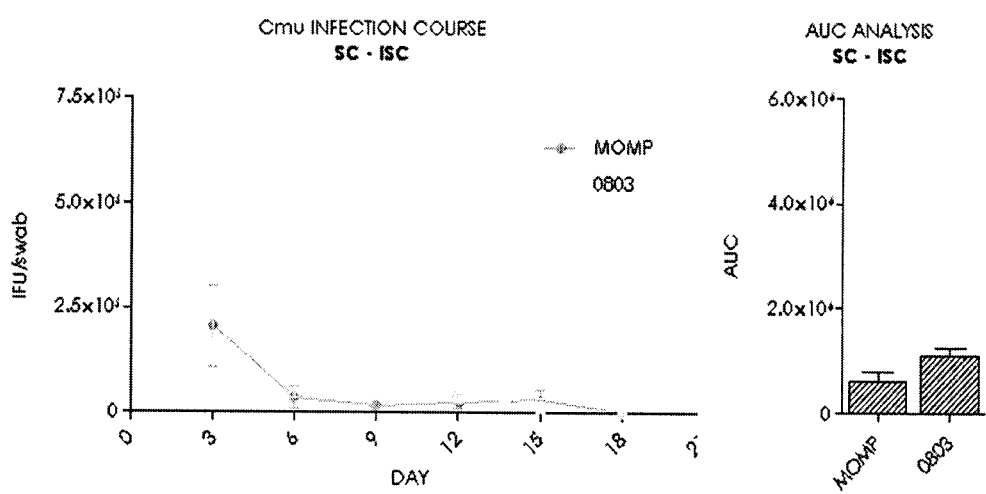

Clearance of Murine *C. trachomatis* (Cmu) from the Vaginal Vault Following a Combination of Subcutaneous (SC) Immunization with Isomatrix Adjuvant (10 ug) and Live Challenge with Cmu (FIG. 8)

Mice were immunized with either rMOMP or rCpn0803 as described in FIG. 1, then challenged with $5 \times 10^4$ IFU Cmu intravaginally on day 42. Vaginal swabs were collected every 3 days for 21 days to assess the level of Cmu infection in McCoy cells and expressed as IFU/swab (left panel). The area under the curve (AUC) analysis (right panel) allows comparison of extent of infection by combining the intensity and duration of Cmu infection between groups.

Figure 9:
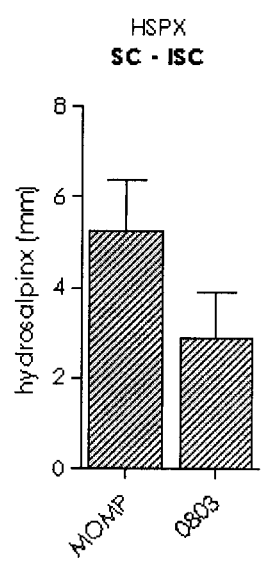

Degree of Genital Tract Pathology in Mice Immunized Subcutaneously (SC) with rMOMP or rCpn0803 and Isomatrix Adjuvant (10 μg) (FIG. 9)

Mice were immunized as described in FIG. 1, challenged with live Cmu, and oviducts were removed 35 days after challenge and assessed for the presence of hydrosalpinx (hspx) which was measured in mm if present.

Figure 10:
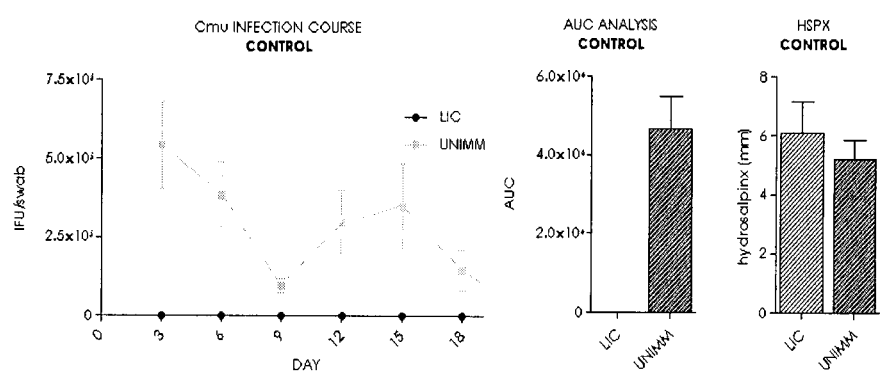

Clearance of Murine *C. trachomatis* (Cmu) from the Vaginal Vault Following Live Infection with Cmu in the Absence of Immunization (FIG. 10)

Following challenge with $5 \times 10^4$ IFU Cmu intravaginally on day 42 vaginal swabs were collected every 3 days for 21 days to assess the level of Cmu infection in McCoy cells and expressed as IFU/swab (left panel). The area under the curve (AUC) analysis (right panel) allows comparison of extent of infection by combining the intensity and duration of Cmu infection between groups.

Figure 11:
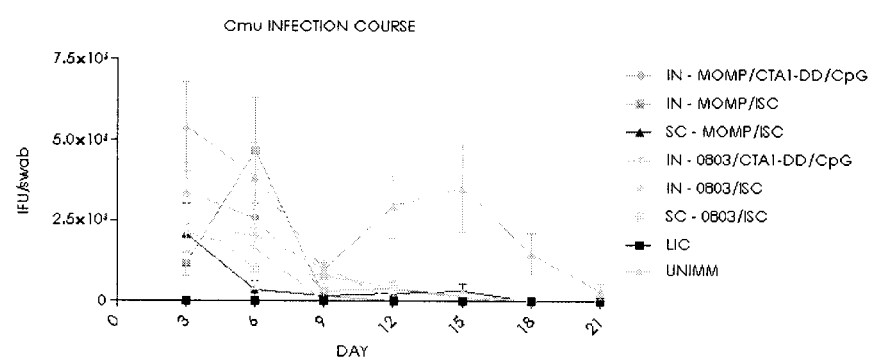

Clearance of Murine *C. trachomatis* (Cmu) from the Vaginal Vault in Immunized and Un-Immunized Animals (UNIMM) (FIG. 11)

FIG. 11 shows compiled data from FIGS. 3, 5, 7, 8, and 10. Following intranasal (IN) or subcutaneous (SC) immunization with rMOMP or rCpn0803 and either CTA-1 DD/CpG adjuvant (5 ug each) or Isocomatrix adjuvant as described in FIG. 1 and were challenged with Cmu as described in FIG. 3. Vaginal swabs were collected every 3 days for 21 days to assess the level of Cmu infection in McCoy cells and expressed as IFU/swab (left panel).

Figure 12:
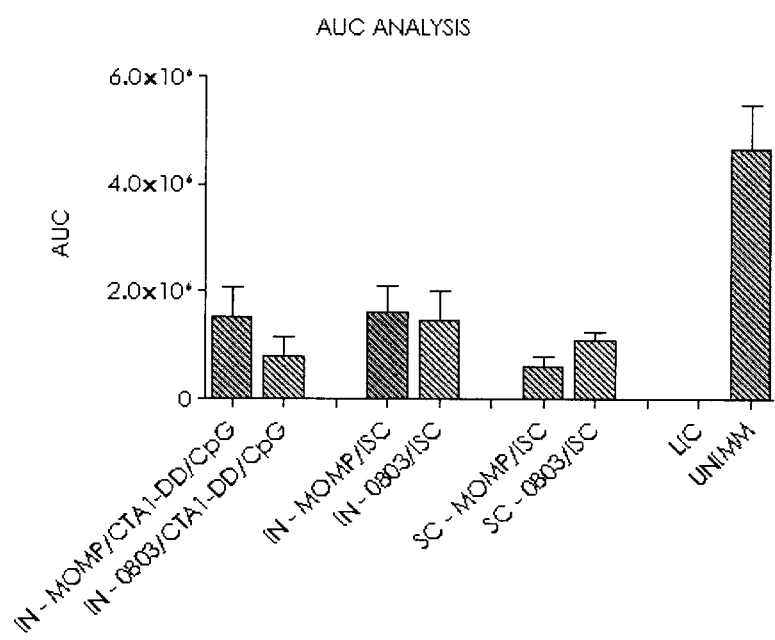

Area Under the Curve Analysis for Various Immunization Routes and Various Adjuvants (FIG. 12)

Data compiled from FIGS. 3, 5, 8, and 10 and compared with unimmunized animals (UNIMM).

Figure 13:
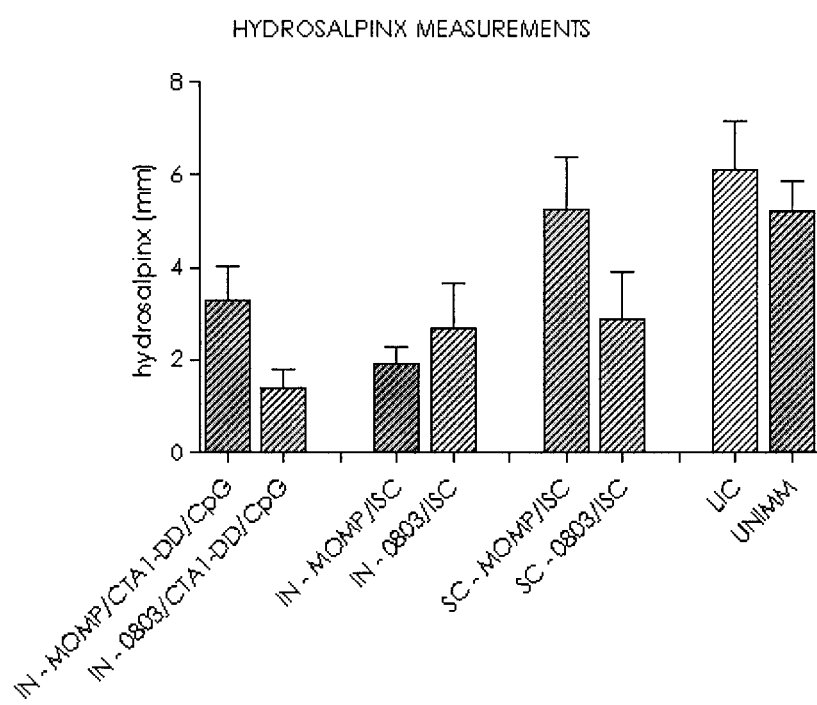

Degree of Genital Tract Pathology in Mice Immunized Subcutaneously (SC) or Intranasally (IN) with Either rMOMP or rCpn0803 and Either CTA1-DD/CpG Adjuvant or Isomatrix Adjuvant or Unimmunized Mice (UNIMM) (FIG. 13)

Graph represents compiled data from FIGS. 4, 6, 9, and 10. Mice were immunized as described in FIG. 1, challenged with live Cmu, and oviducts were removed 35 days after challenge and assessed for the presence of hydrosalpinx (hspx) which was measured in mm if present.

Figure 14:
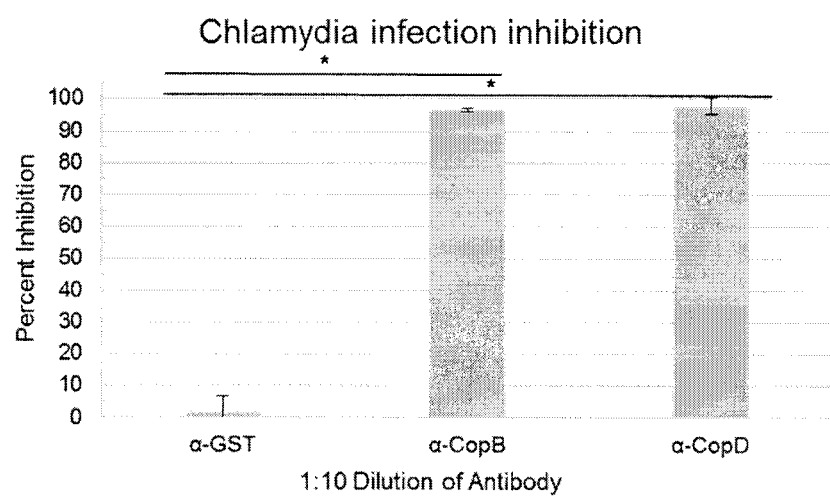

Percent Inhibition of *Chlamydia* Infection when Pre Incubated with Antibodies to CopB and CopD (FIG. 14)

*Chlamydia* pneumonia was incubated with control antibody (anti-GST), anti-CopB or anti-CopD at a 1:10 dilution prior to infection. Percent inhibition of infection is shown as compared to infection alone. Experiments were performed in triplicate; error bars represent 2 standard deviations.

Example 2. Characterization of CopB

FIGS. 15 to 20 show that CopB is associated with the T3SS, and is most likely a translocator protein. The chaperone binding domain is characteristic of translocator proteins, and using a peptide mimetic it is shown that the chaperone binding domain can prevent *Chlamydia* infection. In addition, it is demonstrated that α-CopB antibody can inhibit infection, showing that CopB can function as a vaccine to protect against *Chlamydia* infections.

TABLE 2

Comparison of putative chaperone binding domains between Chlamydiaceae family members and other T3SS containing Gram-negative bacteria. Putative chaperone binding domains were identified within the N-terminal regions of orthologous proteins to CopB from *C. pneumoniae*. P1, P3, P6, represent positions 1, 3, and 6, respectively of the PxLxxP motif. Percent identity refers to amino acid sequence identity comparing full length CopB to full length sequences of orthologous proteins.

|  | P1 |  | P3 |  |  | P6 |  |
|---|---|---|---|---|---|---|---|
| CopB (*C. pneumoniae*) | P | E | L | P | K | P | 100% |
| CT578 (*C. trachomatis* serovar D) | P | G | L | P | K | P | 52% |
| SseC like family protein (*C. psittaci*) | P | D | L | P | K | P | 53% |
| TC_0867 (*C. muridarum*) | P | G | L | P | K | P | 50% |
| CPE1_0913 (*C. pecorum*) | P | E | L | T | P | P | 53% |
| CAB923 (*C. abortus* S26/3) | P | D | L | P | K | P | 54% |
| PopB (*Y. enterocolitica*) | P | A | L | G | R | P | 18% |
| IpaB (*S. dysenteriae*) | P | E | L | K | A | P | 17% |

Example 3. Trivalent Vaccine

A trivalent antigen composed of full length CT584 followed by the N-terminal 100 amino acids of CT578 and the N-terminal 100 amino acids of CT579 was constructed (FIG. 20). The construct was cloned into a pETDuet-1 expression vector for expression in *E. coli*.

Three consecutive restriction digestions and ligations were used to insert CT584, CT578(1-100), CT579(1-100) into MCS1, which encodes an N-terminal 6×-His tag, yielding the following ~43 kDa fusion protein: 6×His-His-CT584-CT578(1-100)-CT579(1-100).

FIG. 21 shows the presence of neutralizing antibody in vaccinated mice. Serum from mice immunized with CpG+ CT584-CT578(1-100)-CT579(1-100) trivalent antigen (vaccinated group) reduced infection by 78% compared to the unvaccinated PBS control group. Each bar graph represents the mean percent reduction for the 5 mice in each group. Infection was assessed by immunofluorescence.

FIG. 22 shows representative urogenital tract pathology in CpG+ trivalent antigen vaccinated mice compared to PBS vaccinated mice following *Chlamydia* infection. The pictures are representative images from two groups of five mice who were vaccinated with PBS or CpG+CT584-CT578(1-100)-CT579(1-100) trivalent antigen and then challenged with *Chlamydia trachomatis* strain *C. muridarum*. Note the presence of uterine horn and hydrosalpinx pathology in the PBS vaccinated mouse, which is which is reduced or almost absent in the CpG+ trivalent antigen vaccinated mouse.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents, and patent applications are herein incorporated by reference in their entirety to the same extent as if each individual publication, patent or patent application was specifically and individually indicated to be incorporated by reference in its entirety.

REFERENCES

James A B, Simpson T Y, Chamberlain W A. *Chlamydia* prevalence among college students: reproductive and public health implications. Sex Transm Dis. 2008 June; 35(6):529-32.

Senior K. *Chlamydia*: a much underestimated STI. Lancet Infect Dis. 2012 July; 12(7):517-8.

Global WHO Alliance for the Elimination of Blinding Trachoma by 2020. Wkly Epidemiol Rec. 2012 Apr. 27; 87(17):161-8.

Polkinghorne A, Schmidt-Posthaus H, Meijer A, Lehner A, Vaughan L. Novel Chlamydiales associated with epitheliocystis in a leopard shark Triakis semifasciata. Dis Aquat Organ. 2010 Jul. 26; 91(1):75-81.

Fields, K., and T. Hackstadt. Evidence for the secretion of *Chlamydia trachomatis* CopN by a type III secretion mechanism. 2000. Mol. Microbiol. 38: 1048-1060.

Johnson D L, Stone C B, Mahony J B. Interactions between CdsD, CdsQ, and CdsL, three putative *Chlamydophila pneumoniae* type III secretion proteins. J Bacteriol. 2008 April; 190(8):2972-80. Epub 2008 Feb. 15.

Stone C B, Johnson D L, Bulir D C, Gilchrist J D, Mahony J B. Characterization of the putative type III secretion ATPase CdsN (Cpn0707) of *Chlamydophila pneumoniae*. J Bacteriol. 2008 October; 190(20):6580-8. Epub 2008 Aug. 15.

Stone C B, Bulir D C, Gilchrist J D, Toor R K, Mahony J B. Interactions between flagellar and type III secretion proteins in *Chlamydia pneumoniae*. BMC Microbiol. 2010 Jan. 22; 10:18.

Stone C B, Bulir D C, Emdin C A, Pirie R M, Porfilio E A, Slootstra J W, Mahony J B. *Chlamydia Pneumoniae* CdsL Regulates CdsN ATPase Activity, and Disruption with a Peptide Mimetic Prevents Bacterial Invasion. Front Microbiol. 2011; 2:21. Epub 2011 Feb. 14.

Toor R K, Stone C B, Gilchrist, J D, Mahony J B. *Chlamydia pneumoniae* CdsQ functions as a multi-cargo transport protein, delivering chaperone-effector complexes to CdsN the type III secretion ATPase. Translational Biomedicine 2012 3(1-2) doi: 10.3823/430 1-11.

Clifton, D., K. Fields, S. Grieshaber, C. Dooley, E. Fischer, D. Mead, R. Carabeo, and T. Hackstadt. A chlamydial type III translocated protein is tyrosine-phosphorylated at the site of entry and associated with recruitment of actin. 2004. Proc. Natl. Acad. Sci. USA 101:10166-10171.

Coombes, B., and J. Mahony. Identification of MEK- and phosphoinositide-3-kinase-dependant signaling as essential events during *Chlamydia pneumoniae* invasion of HEp2 cells. 2002 Cell. Microbiol. 4:447-460.

Hybiske K, Stephens R S. Mechanisms of host cell exit by the intracellular bacterium *Chlamydia*. Proc Natl Acad Sci USA. 2007 Jul. 3; 104(27):11430-5. Epub 2007 Jun. 25.

Beeckman D S, Vanrompay D C. Bacterial secretion systems with an emphasis on the chlamydial Type III secretion system. Curr Issues Mol Biol. 2010; 12(1)17-41. Epub 2009 Jul. 16.

Galan, J., and H. Wolf-Watz. Protein delivery into eukaryotic cells by type III secretion machines. 2006. Nature 444:567-573.

Ghosh, P. Process of protein transport by the type III secretion system. 2004 Microbiol. Mol. Biol. Rev. 68:771-795.

Markham A P, Jaafar Z A, Kemege K E, Middaugh C R, Hefty P S. Biophysical characterization of *Chlamydia trachomatis* CT584 supports its potential role as a type III secretion needle tip protein. Biochemistry. 2009 Nov. 3; 48(43):10353-61.

Stone C B, Sugiman-Marangos S, Bulir D C, Clayden R C, Leighton T L, Slootstra J W, Junop M S, Mahony J B. Structural characterization of a novel *Chlamydia pneumoniae* type III secretion-associated protein, Cpn0803. PLoS One. 2012; 7(1):e30220. Epub 2012 Jan. 17.

Goure J, Pastor A, Faudry E, Chabert J, Dessen A, Attree I. The V antigen of *Pseudomonas aeruginosa* is required for assembly of the functional PopB/PopD translocation pore in host cell membranes. Infect Immun. 2004 August; 72(8):4741-50.

Goure J, Broz P, Attree O, Cornelis G R, Attree I. Protective anti-V antibodies inhibit *Pseudomonas* and *Yersinia* translocon assembly within host membranes. J Infect Dis. 2005 Jul. 15; 192(2):218-25. Epub 2005 Jun. 7.

Zauberman A, Cohen S, Levy Y, Halperin G, Lazar S, Velan B, Shafferman A, Flashner Y, Mamroud E. Neutralization of *Yersinia pestis*-mediated macrophage cytotoxicity by anti-LcrV antibodies and its correlation with protective immunity in a mouse model of bubonic plague. Vaccine. 2008 Mar. 20; 26(13):1616-25. Epub 2008 Feb. 6.

Huston W M, Harvie M, Mittal A, Timms P, Beagley K W. Vaccination to protect against infection of the female reproductive tract. Expert Rev Clin Immunol. 2012 January; 8(1):81-94.

Kari L, Whitmire W M, Crane D D, Reveneau N, Carlson J H, Goheen M M, Peterson E M, Pal S, de la Maza L M, Caldwell H D. *Chlamydia trachomatis* native major outer membrane protein induces partial protection in nonhuman primates: implication for a trachoma transmission-blocking vaccine. J Immunol. 2009 Jun. 15; 182(12):8063-70.

Carey A J, Timms P, Rawlinson G, Brumm J, Nilsson K, Harris J M, Beagley K W. A multi-subunit chlamydial vaccine induces antibody and cell-mediated immunity in immunized koalas (*Phascolarctos cinereus*): comparison of three different adjuvants. Am J Reprod Immunol. 2010 February; 63(2):161-72.

Singh S R, Hulett K, Pillai S R, Dennis V A, Oh M K, Scissum-Gunn K. Mucosal immunization with recombinant MOMP genetically linked with modified cholera toxin confers protection against *Chlamydia trachomatis* infection. Vaccine. 2006 Feb. 20; 24(8):1213-24. Epub 2005 Sep. 12.

Holder I A, Neely A N, Frank D W. PcrV immunization enhances survival of burned *Pseudomonas aeruginosa*-infected mice. Infect Immun. 2001 September; 69(9): 5908-10.

Imamura Y, Yanagihara K, Fukuda Y, Kaneko Y, Seki M, Izumikawa K, Miyazaki Y, Hirakata Y, Sawa T, Wiener-Kronish J P, Kohno S. Effect of anti-PcrV antibody in a murine chronic airway *Pseudomonas aeruginosa* infection model. Eur Respir J. 2007 May; 29(5):965-8. Epub 2007 Feb. 14.

The invention claimed is:

1. A fusion protein comprising (a) a polypeptide comprising the amino acid sequence of SEQ ID NO: 1 or SEQ ID NO: 4, or an amino acid sequence having at least 90% sequence identity to SEQ ID NO: 1 or SEQ ID NO: 4, (b) a polypeptide comprising amino acid residues 1-100 of the amino acid sequence of SEQ ID NO: 2 or SEQ ID NO: 5 or an amino acid sequence having at least 90% sequence identity to SEQ ID NO: 2 or SEQ ID NO: 5 and (c) a polypeptide-comprising amino acid residues 1-100 of the amino acid sequence of SEQ ID NO: 3 or SEQ ID NO: 6 or an amino acid sequence having at least 90% sequence identity to SEQ ID NO: 3 or SEQ ID NO: 6.

2. A composition comprising the fusion protein of claim 1, wherein the composition further comprises an adjuvant.

3. The composition of claim 2, wherein the adjuvant is CTA-DD, Iscomatrix, interleukin-12 (IL-12), CpG oligodeoxynucleotides, alum, Montanide ISA 720 or any combination thereof.

4. The composition of claim 2, wherein the composition is formulated for oral, intranasal, intravaginal, ocular or systemic administration.

5. The fusion protein of claim 1, comprising (a) a polypeptide comprising the amino acid sequence of SEQ ID NO: 4, (b) a polypeptide comprising amino acid residues 1-100 of SEQ ID NO: 5 and (c) a polypeptide comprising amino acid residues 1-100 of SEQ ID NO: 6.

* * * * *